US009370478B2

(12) United States Patent
Bonner et al.

(10) Patent No.: US 9,370,478 B2
(45) Date of Patent: *Jun. 21, 2016

(54) SKIN CARE COMPOSITIONS CONTAINING COTTON AND CITRUS-DERIVED MATERIALS

(71) Applicant: JOHNSON & JOHNSON CONSUMER INC., Skillman, NJ (US)

(72) Inventors: Patricia Bonner, Branchburg, NJ (US); Claudia Kaminski, Milford, NJ (US); Danielle Lima Lorenzetti, Jacarei/SP (BR); Prithwiraj Maitra, Bella Mead, NJ (US); Juliana Salles Moscardi, Sao Jose dos Campos/SP (BR); Jeffrey M. Wu, Princeton, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 149 days.

This patent is subject to a terminal disclaimer.

(21) Appl. No.: 14/060,901

(22) Filed: Oct. 23, 2013

(65) Prior Publication Data
US 2014/0134219 A1    May 15, 2014

Related U.S. Application Data

(63) Continuation-in-part of application No. 13/799,467, filed on Mar. 13, 2013, now abandoned.

(60) Provisional application No. 61/724,646, filed on Nov. 9, 2012.

(51) Int. Cl.
*A61K 8/73* (2006.01)
*A61Q 5/12* (2006.01)
(Continued)

(52) U.S. Cl.
CPC .................. *A61K 8/731* (2013.01); *A61K 8/027* (2013.01); *A61Q 5/12* (2013.01); *A61Q 19/008* (2013.01); *A61Q 19/10* (2013.01); *A61K 2800/412* (2013.01); *A61K 2800/546* (2013.01)

(58) Field of Classification Search
None
See application file for complete search history.

(56) References Cited

U.S. PATENT DOCUMENTS

| 1,873,030 | A | 8/1932 | Quinn |
| 2,129,264 | A | 9/1938 | Baxter et al. |

(Continued)

FOREIGN PATENT DOCUMENTS

| EP | 819787 A | 1/1998 |
| EP | 829259 A | 3/1998 |

(Continued)

OTHER PUBLICATIONS

International Cosmetic Ingredient Dictionary and Handbook, vol. 2, 7th edition, pp. 1-42 (1990).*

(Continued)

*Primary Examiner* — Ernst V Arnold
*Assistant Examiner* — Kyung Sook Chang

(57) ABSTRACT

The compositions and methods of this invention relate to skin care compositions containing: (a) hydrophobic and hydrophilic, linear cellulose particles having an average length of from about 1 to about 1000 μm, a particle aspect ratio from about 1000 to about 2 and a thickness of from about 1 to about 500 μm; (b) amphiphilic linear cellulose particles derived from sources selected from the following group: citrus pulp, sugar beet pulp, banana pulp, mango pulp, apple pulp, passion fruit pulp and tomato pulp and the like, said particles having an average size of from about 1 to about 1000 μm, a particle aspect ratio from about 1000 to about 2 and a thickness of from about 1 to about 500 μm; wherein the ratio of ingredient (b) to ingredient (a) is from about 1:10 to about 10:1; and a cosmetically acceptable carrier.

17 Claims, 17 Drawing Sheets

(51) Int. Cl.
  *A61Q 19/10* (2006.01)
  *A61K 8/02* (2006.01)
  *A61Q 19/00* (2006.01)

(56) References Cited

U.S. PATENT DOCUMENTS

| | | | |
|---|---|---|---|
| 2,178,353 | A | 10/1939 | Werntz |
| 2,774,786 | A | 12/1956 | Erickson |
| 2,813,898 | A | 11/1957 | Gaertner |
| 2,828,332 | A | 3/1958 | Gaertner |
| 3,278,383 | A | 10/1966 | White et al. |
| 3,318,817 | A | 5/1967 | Smith, Jr. |
| 3,755,560 | A | 8/1973 | Dickerty et al. |
| 4,215,064 | A | 7/1980 | Lindemann et al. |
| 4,233,192 | A | 11/1980 | Lindemann et al. |
| 4,254,105 | A | 3/1981 | Fukuda |
| 4,272,514 | A | 6/1981 | Spence |
| 4,372,869 | A | 2/1983 | Lindemann et al. |
| 4,380,637 | A | 4/1983 | Lindemann et al. |
| 4,382,036 | A | 5/1983 | Lindemann et al. |
| 4,421,769 | A | 12/1983 | Dixon et al. |
| 4,490,764 | A | 12/1984 | Butz |
| 4,559,243 | A | 12/1985 | Passler et al. |
| 4,606,958 | A | 8/1986 | Haq et al. |
| 4,617,414 | A | 10/1986 | Lukenbach et al. |
| 4,960,764 | A | 10/1990 | Figueroa, Jr. et al. |
| 5,415,804 | A | 5/1995 | Minami et al. |
| 5,654,362 | A | 8/1997 | Schulz, Jr. et al. |
| 5,763,497 | A | 6/1998 | Ikeda et al. |
| 5,830,485 | A | 11/1998 | Gueret et al. |
| 5,891,424 | A | 4/1999 | Bretzler et al. |
| 5,919,437 | A | 7/1999 | Lee et al. |
| 5,964,983 | A | 10/1999 | Dinand et al. |
| 5,965,146 | A | 10/1999 | Franzke et al. |
| 5,976,514 | A | 11/1999 | Guskey et al. |
| 6,001,338 | A | 12/1999 | Mondet |
| 6,060,546 | A | 5/2000 | Powell et al. |
| 6,123,951 | A | 9/2000 | Gueret et al. |
| 6,294,509 | B1 | 9/2001 | Meiwa et al. |
| 6,342,237 | B1 | 1/2002 | Bara |
| 6,491,931 | B1 | 12/2002 | Collin |
| 6,503,520 | B1 | 1/2003 | Afriat |
| 6,534,071 | B1 | 3/2003 | Tournilhac et al. |
| 6,607,734 | B1 | 8/2003 | Afriat |
| 6,620,419 | B1 | 9/2003 | Lintner |
| 6,656,487 | B2 | 12/2003 | Afriat et al. |
| 6,689,345 | B2 | 2/2004 | Jager Lezer |
| 6,906,106 | B2 | 6/2005 | Chevalier |
| 7,094,317 | B2 | 8/2006 | Lundberg et al. |
| 7,378,103 | B2 | 5/2008 | Kanji et al. |
| 7,594,619 | B2 | 9/2009 | Ghere, Jr. et al. |
| 7,780,971 | B2 | 8/2010 | Chevalier et al. |
| 7,803,403 | B2 | 9/2010 | Librizzi et al. |
| 7,820,151 | B2 | 10/2010 | de la Poterie et al. |
| 7,846,461 | B2 | 12/2010 | Hwang et al. |
| 8,029,773 | B2 | 10/2011 | Loginova et al. |
| 8,105,691 | B2 | 1/2012 | Takeuchi et al. |
| 8,772,359 | B2 | 7/2014 | Swazey |
| 8,894,980 | B2 | 11/2014 | Kawasaki et al. |
| 8,894,981 | B2 | 11/2014 | Shimizu et al. |
| 9,018,189 | B2 | 4/2015 | Herranen et al. |
| 9,045,716 | B2 | 6/2015 | Swazey et al. |
| 9,089,502 | B2 | 7/2015 | Bui et al. |
| 2002/0028222 | A1 | 3/2002 | Afriat |
| 2002/0031533 | A1 | 3/2002 | Afriat |
| 2002/0182238 | A1 | 12/2002 | Creton |
| 2002/0192251 | A1 | 12/2002 | Collin |
| 2002/0197289 | A1 | 12/2002 | Chevalier et al. |
| 2003/0024556 | A1 | 2/2003 | Guiramand et al. |
| 2003/0086951 | A9 | 5/2003 | Piot et al. |
| 2003/0086962 | A1 | 5/2003 | Westerfield et al. |
| 2004/0142008 | A1 | 7/2004 | Chevalier et al. |
| 2004/0161435 | A1 | 8/2004 | Gupta |
| 2005/0002996 | A1 | 1/2005 | Sojka |
| 2005/0175650 | A1 | 8/2005 | Hadasch et al. |
| 2005/0191259 | A1 | 9/2005 | Feng |
| 2006/0008485 | A1 | 1/2006 | Ferone et al. |
| 2006/0029625 | A1 | 2/2006 | Niebauer |
| 2006/0182699 | A1 | 8/2006 | Taylor et al. |
| 2006/0246027 | A1 | 11/2006 | Tanner |
| 2006/0257348 | A1 | 11/2006 | Walters et al. |
| 2006/0275232 | A1 | 12/2006 | Chevalier |
| 2007/0111910 | A1 | 5/2007 | Walters et al. |
| 2007/0141095 | A1 | 6/2007 | Simonnet |
| 2008/0138368 | A1 | 6/2008 | Lezer |
| 2008/0241087 | A1 | 10/2008 | Farsedakis et al. |
| 2009/0263342 | A1 | 10/2009 | Glenn, Jr. et al. |
| 2009/0269299 | A1 | 10/2009 | Cassin |
| 2009/0269376 | A1 | 10/2009 | Lundberg et al. |
| 2010/0009891 | A1 | 1/2010 | Canto et al. |
| 2010/0221294 | A1 | 9/2010 | Kurek et al. |
| 2010/0286583 | A1 | 11/2010 | Torres |
| 2011/0081388 | A1 | 4/2011 | Oh et al. |
| 2011/0223223 | A1 | 9/2011 | Murata et al. |
| 2011/0250250 | A1 | 10/2011 | Kishida et al. |
| 2011/0319306 | A1 | 12/2011 | Walters et al. |
| 2011/0319307 | A1 | 12/2011 | Gunn et al. |
| 2012/0142909 | A1 | 6/2012 | Lundberg |
| 2013/0340781 | A1 | 12/2013 | Liebel et al. |
| 2014/0134219 | A1 | 5/2014 | Bonner et al. |
| 2014/0286887 | A1 | 9/2014 | Sandler et al. |
| 2014/0357721 | A1 | 12/2014 | Shirao et al. |
| 2015/0037383 | A1 | 2/2015 | Bonner et al. |
| 2015/0040933 | A1 | 2/2015 | Bonner et al. |
| 2015/0110841 | A1 | 4/2015 | Wiechers et al. |
| 2015/0164779 | A1 | 6/2015 | Botto et al. |
| 2015/0297469 | A1 | 10/2015 | Hayashi et al. |

FOREIGN PATENT DOCUMENTS

| | | |
|---|---|---|
| EP | 1813252 A | 8/2007 |
| EP | 2332519 A1 | 6/2011 |
| EP | 2382961 A | 11/2011 |
| EP | 2907498 A | 8/2015 |
| JP | S63238008 A | 10/1988 |
| JP | 1990-174709 A | 7/1990 |
| JP | H02174709 A | 7/1990 |
| JP | H11152206 A | 6/1999 |
| JP | 2007056236 A | 3/2007 |
| KR | 20090056295 A | 6/2009 |
| WO | WO 2008/129955 A | 10/2008 |
| WO | WO 2009/037347 A | 3/2009 |
| WO | WO 2011/105535 A | 9/2011 |
| WO | WO 2012/133018 A | 10/2012 |
| WO | WO 2013/039483 A | 3/2013 |
| WO | WO 2013/186715 A | 12/2013 |
| WO | WO 2013/186720 A | 12/2013 |
| WO | WO 2014/185284 A | 11/2014 |

OTHER PUBLICATIONS

Awapaper, "Regenerated Fibers" ([retrieved from on-line website: http://www.awapaper.co.jp/e/products/detail/s_m01c.html, last access date: Mar. 2, 2016]).*
Olson Eric "Particle shaped factors and their use in image analysis part II: Practical Applications" Autumn 2011.
International Search Report dated Feb. 26, 2014, for corresponding PCT/US2013/068697.
Fiberstar: "Imulsi-Fi", Imulsi-Fi A30 Information Booklet, Apr. 1, 2012, pp. 1-28 (XP007920784).
U.S. Appl. No. 14/259,463, filed Apr. 23, 2014, Bonner et al.
U.S. Appl. No. 14/259,224, filed Apr. 23, 2014, Bonner et al.
U.S. Appl. No. 13/799,293, filed Mar. 13, 2013, Bonner et al.
U.S. Appl. No. 13/673,430, filed Nov. 9, 2012, Bonner et al.
U.S. Appl. No. 13/799,365, filed Mar. 13, 2013, Bonner et al.
U.S. Appl. No. 13/673,477, filed Nov. 9, 2012, Bonner et al.
U.S. Appl. No. 13/799,467, filed Mar. 13, 2013, Bonner et al.
U.S. Appl. No. 61/724,646, filed Nov. 9, 2012, Bonner et al.
*The International Cosmetic Ingredient Dictionary and Handbook*, 7th Edition (1997) ("ICI Handbook"), eds. Wenninger and McEwen, The Cosmetic, Toiletry and Fragrance Assoc., Washington, D.C., pp. 1612, 1613, 1626, 1650-1667, 1673-1686 and 1693-1697.

(56) References Cited

OTHER PUBLICATIONS

McCutcheon's Detergents and Emulsifiers, North American Edition (1986), pp. 317-324.

Sagarin, *Cosmetics, Science and Technology*, 2nd Edition (1972), vol. 1, pp. 32-43 and pp. 72-73.

Thielmann et al., "Determination of the surface energy distributions of different processed lactose", *Drug Development and Industrial Pharmacy*, 33(11):1240-53, Nov. 2007.

Yla-Maihaniemi et al., "Inverse gas chromatographic method for measuring the dispersive surface energy distribution for particulates", *Langmuir*, vol. 24(17):9551-7, Sep. 2, 2008.

\* cited by examiner

IR Spectra of Cotton Powders and Cellulose

SKIN CARE COMPOSITIONS CONTAINING COTTON AND CITRUS-DERIVED MATERIALS

This application is a continuation-in-part application of U.S. application Ser. No. 13/799,467 filed Mar. 13, 2013, which claims the benefit of U.S. provisional application 61/724,646 filed Nov. 9, 2012, the complete disclosures of which are hereby incorporated herein by reference for all purposes.

FIELD OF THE INVENTION

The compositions of this invention relate to skin care compositions that reduce the presence of oil-related substances on skin and that contain hydrophobic and/or hydrophilic linear cellulose particles and amphiphilic linear cellulose particles.

BACKGROUND OF THE INVENTION

Oily skin is shiny, thick and dull colored. Often, chronically oily skin has coarse pores and pimples and other embarrassing blemishes. Furthermore, chronically oily skin can be prone to developing blackheads. In this type of skin, the oil-producing sebaceous glands are overactive and produce more oil than is needed. The oil flows out of the follicles and gives the skin an undesirable greasy shine. The pores are enlarged and the skin has a coarse look. While oily skin is common in teenagers, it can occur at any age.

Generally, individuals having oily skin attempt to treat areas of oiliness in order to prevent outbreaks of acne and to diminish shininess. The conventional treatments available include soaps or surfactant based cleansers, astringents with alcohol and clay or mud masks. Oil absorbing materials such as clay or salt have also been used to attempt to treat this condition.

Individuals having oily or shiny skin conditions prefer a treatment that can remove the shine without drying the skin. However, there is a lack of effective skin care products on the market today that address this consumer need. Oil absorbing particles s such as silica, aluminum starch, and talc have been used in the cleansing products to help dry the skin surface oil, but they also tend to dry the skin and oily and shiny skin tend to come back quickly, usually in two to three hours.

Thus, it would be desirable to have compositions and methods of treatment that address the condition of oily skin while keeping skin hydrated.

SUMMARY OF THE INVENTION

The compositions and methods of this invention relate to skin care compositions comprising (a) linear cellulose particles selected from the group consisting of hydrophobic and hydrophilic linear cellulose particles the linear hydrophobic and hydrophilic cellulose particles having an average length of from about 1 to about 1000 μm, a particle aspect ratio from about 1000 to about 2 and a thickness of from about 1 to about 500 μm (ingredient (a)); (b) amphiphilic linear cellulose particles derived from sources selected from the group consisting of citrus pulp, sugar beet pulp, banana pulp, mango pulp, apple pulp, passion fruit pulp and tomato pulp, the amphiphilic linear cellulose particles having an average size of from about 1 to about 1000 μm, a particle aspect ratio from about 1000 to about 2 and a thickness of from about 1 to about 500 μm (ingredient b); and a cosmetically acceptable carrier, wherein the ratio of ingredient (b) to ingredient (a) is from about 1:10 to about 10:1. More preferably, the ratio of ingredient (b) to ingredient (a) is from about 1:1 to about 4:1. Most preferably, the ratio is from about 1:1 to about 2:1.

The compositions of this invention may be formulated and used as leave-on compositions such as moisturizers, foundations, or the like or they may be formulated and may also be used as rinse-off compositions such as cleanser, scrubs, masques or the like. Surprisingly, the compositions of this invention containing both ingredient (a) and ingredient (b) have an unexpectedly faster and higher level of water absorbing and retention properties as compared with compositions containing either ingredient (a) or ingredient (b) alone.

DETAILED DESCRIPTION OF THE INVENTION

Figure 1:
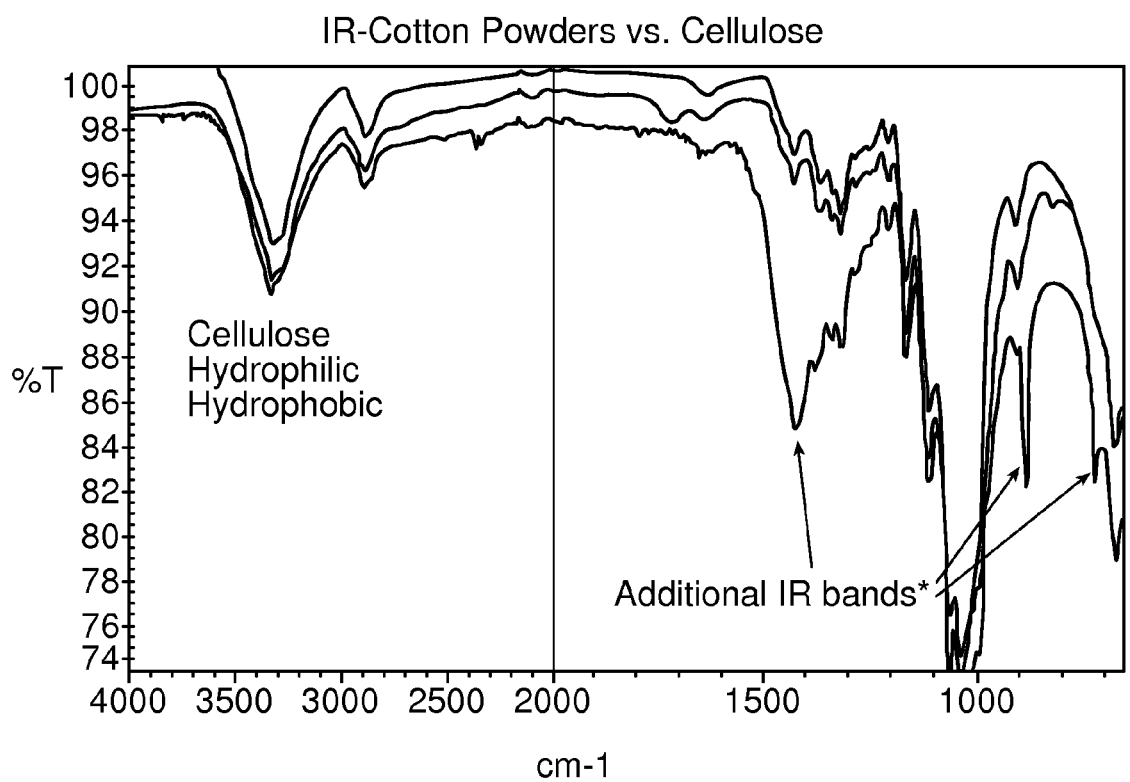
FIG. 1 is a graph of Infrared spectra of various cotton powders and cellulose particles.

As used herein, the term "hydrophobic" means materials having a surface contact angle with squalene of less than 40 degrees and/or a surface contact angle with water of greater than 90 degrees. The term "amphiphilic" means a compound or material that possesses both hydrophilic (i.e., water-loving) and lipophilic or hydrophobic (i.e., fat-loving) properties. Such materials generally comprise molecules having a polar water-soluble group attached to a water-insoluble hydrocarbon chain and have a surface contact angle with water of greater than 90 degrees.

As used herein, the term "hydrophilic" means materials having a surface contact angle with water of less than 90 degrees. The term "surface contact angle" means the internal angle between a surface and a liquid droplet resting on that surface. Surface tension (liquid) or surface free energy (solid) is considered to be a resulting balance between the molecular interactions of the liquid-liquid and air-liquid or solid-solid and air-solid phase at the interfacial layer. The term "contact angle" is a convenient and useful parameter to determine the surface free energy and wettability of any given solid surface due to the non-deformability of the solid. The contact angle is determined by measuring the angle formed between substrate surface where a liquid droplet is placed and the tangent to the drop surface from the contact point. High contact angles correspond to poor wetting of the surface by the liquid and low contact angles signify good wetting. If a liquid spreads on the surface, the contact angle is considered to be zero and complete wetting is said to occur.

Contact angle measurements can be employed to determine the wettability of human skin by a variety of liquids, including hydrophobic liquids such as squalene and hydrophilic liquids, including water. A smaller contact angle with a non-polar liquid (such as squalene) corresponds to a more hydrophobic material, while a smaller contact angle with water corresponds to a more hydrophilic material.

In accordance with the methods and compositions of this invention, the contact angle with water of the hydrophobic, linear cellulose particles is preferably greater than 90 degrees, preferably greater than 100 degrees and more preferably greater than 120 degrees.

In accordance with the methods and compositions of this invention, the contact angle with water of the hydrophilic, linear cellulose particles is preferably less than 90 degrees, preferably less than 60 degrees.

Certain materials, termed amphiphilic, exhibit both hydrophobic and hydrophilic behaviors because of the presence of a hydrophobic backbone structure with hydrophilic molecular functional groups attached on the side of the hydrophobic backbone. Such materials can have a large contact angle with water droplets e.g. large than 90 degrees, while smaller particles are attracted to or climb water droplets. It can also consist of a hydrophilic backbone structure with hydrophobic materials coated partially on hydrophilic bulk materials or particles.

As used herein, the term "oil absorption capacity and retention" refers to the weight percentage of the oil absorbed by the hydrophobic and hydrophilic linear cellulose particles useful in the compositions and methods of this invention. High oil absorption capacity and retention corresponds to an increased hydrophobic property. The oil absorption capacity and retention of the hydrophobic and hydrophilic linear cellulose particles of the compositions of this invention is preferably from about 150 to about 500, and more preferably from about 300 to about 500% by weight oil/weight particles.

As used herein, the term "particle" means a small localized object to which can be ascribed physical properties such as volume or mass. As used herein, the terms "powder(s)" and "fibers" are used synonymously with "particles", as defined herein.

As used herein, the term "linear particle" means a particle having one dimension ("length") that is greater than another dimension ("width"). Linear particles may be measured and defined by size by subjecting such particles to analysis with respect to a series of sieves having different mesh sizes. Generally, a sample of linear particles may have a distribution of particle sizes throughout the sample. Thus, linear particle sizes as expressed herein are expressed as an average particle size and reflect the average length of the particles contained within the sample.

Preferably, the size of linear particles useful in the compositions and methods of this invention is less than about 1000 µm in length, more preferably, it ranges from about 1 to about 1000 µm, and most preferably from about 10 to about 500 µm. The preferred width of linear particles useful in the compositions and methods of this invention are about 5 to about 25 µm. More preferably, they are from about 5 to about 20 µm in width.

As used herein, the term "particle aspect ratio" means the ratio of the length of a particle to its width. Preferably, the particle aspect ratio of the particles useful in the compositions and methods of this invention is from about 2 to about 1000. More preferably, the particle aspect ratio is from about 2 to about 500 and most preferably, from about 5 to about 200.

As used herein, the term "cellulose" refers to a polysaccharide material consisting of long unbranched chains of linked glucose units, having the chemical structure set forth in Formula I below:

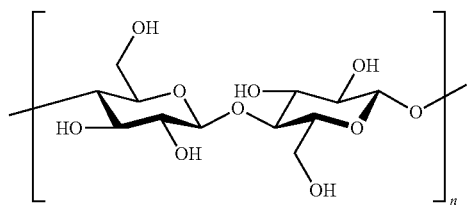

Cellulose, the most abundant biomass on the surface of the earth, has provided mankind with functional, low cost and renewable raw material.

Cellulose particles useful in the compositions and methods of this invention may be derived from cotton, corn, wood pulp and bamboo pulp, silk, cork and the like. Preferably, the cellulose particles useful in the compositions of this invention are derived from cotton. More preferably, the cellulosic particles are from particles recovered from post-industrial scrap. Such scrap is derived from waste or other pre-consumer cotton products from, for example, the apparel, carpet, furniture and household goods industries. Synthetic or regenerated cotton or cellulose materials may also be used as sources for the cellulose particles useful in the compositions and methods of this invention, including rayon, viscose, cellophane, and other cellulosic materials with a uniform and reproducible molecular size and distribution.

The cellulose particles useful in the compositions and methods of this invention may be derived directly from the source plant (referred to herein as, "raw" particles) or may be generated from cloth or nonwoven materials previously formed from plant or cellulose particles (referred to herein as "regenerated" particles). For example, cotton cloth may be processed so as to break the cloth into small particles and/or uniform particles length by cutting the length of the cotton particles from inches to microns. This random-cut particle is available in several grades, white, dark, and unbleached, with average particles lengths from about 1 micron to about 1000 microns and preferably from about 2 microns to about 500 microns.

Typical mechanical milling processes such as those useful in cutting down the size of the cellulose particles useful in the compositions and methods of this invention, for example, are described in U.S. Pat. No. 7,594,619 and U.S. Pat. No. 6,656,487, which are hereby incorporated herein by reference.

Generally, the cellulose particles useful in the compositions of this invention may be processed according to the following methods.

One such method comprises mixing a cellulosic material derived from post-industrial scrap, as defined above, with at least one of grinding aids selected from the group including water, fatty acids, synthetic polymers and organic solvents, and, after mixing, mechanically grinding the mixture.

Another method of obtaining cellulose particles is freezing a cellulosic material derived from post-industrial scrap at a low temperature, and then mechanically grinding said frozen material.

The cellulose particles useful in the compositions and methods of this invention may be further treated with hydrophobic agents to yield hydrophobic cellulose particles. For example, a hydrophobic coating agent may be used to treat the cellulose particles. The hydrophobic coating agent may be any such agent known to one of skill in the art. Preferred hydrophobic coating agents react chemically with the cellulose particle to provide a durable covalent bond thereto and have hydrophobic chemical backbones or substituents that can provide a hydrophobic outer layer around each individual cellulosic particle. The coating agent may react, for example, with hydroxyl groups, available oxygen atoms present on the surface of the cellulose particle being coated.

Hydrophobic agents may include but not limited to low water soluble organic compounds such as metal soap, e.g., a metal myristate, metal stearate, a metal palmitate, a metal laurate or other fatty acid derivatives known to one of skill in the art. Other hydrophobic agents may include an organic wax, such as a synthetic wax like polyethylene or a natural wax like carnauba wax. Hydrophobic agents useful in coating the cellulose particles useful in the compositions and methods of this invention may also be long chain fatty acids or esters such as stearic acid, oleic acid, castor oil, isododecane, silicone, and their derivatives, non-water soluble polymers, e.g. high molecular weight methylcellulose and ethylcellulose, and high molecular water insoluble fluoropolymers etc., polymerized siloxanes or polysiloxanes with the chemical formula [R2SiO]n, where R is an organic group such as methyl, ethyl, or phenyl, such as dimethicone, dimethicone copolyol, dimethicone ester; methicone and their derivatives. Examples of hydrophobic linear cotton particles useful in the present invention include but are not limited to, Cotton Fiber Flock CD60, available from Goonvean Fiber and W200 White Cotton Flock, available from International Fiber Corporation.

A combination of hydrophobic and hydrophiliclinear cellulose particles with amphiphilic linear cellulose particles may also be utilized in accordance with the compositions and methods of this invention. Preferably, such compositions should contain from about 10 and about 20 percent by weight of amphiphilic linear cellulose particles and from about 80 to about 90 percent by weight of hydrophobic and/or hydrophilic linear cellulose particles.

In one embodiment, the amphiphilic linear cellulose particles used in the composition of the invention are highly refined citrus-derived cellulose particles. Such highly refined citrus-derived cellulose particles may be made in accordance with the description set forth in U.S. Pat. No. 7,094,317, which is hereby incorporated herein by reference. A highly refined citrus-derived cellulosic product can be prepared by generally moderate treatment and still provide properties that are equivalent to or improved upon the properties of the best highly refined cellulose products produced from more intense and environmentally unfriendly processes. Fruit or vegetable cells with an exclusively parenchymal cell wall structure can be treated with a generally mild process to form highly absorbent microfibers. Cells from citrus fruit and sugar beets are particularly available in large volumes to allow volume processing to generate highly refined cellulose particles with both unique and improved properties. These exclusively parenchymal microfibers (hereinafter referred to as EPM's) have improved moisture retention and thickening properties that enable the particles to provide unique benefits when combined into edible products (e.g., baked goods, liquefied foods, whipped foods, meats, meat fillers, dairy products, yogurt, frozen food entrees, ice cream, etc.) and in mixtures that can be used to generate edible food products (e.g., baking ingredients, dehydrated or low hydration products).

A process for making HRC cellulose from parenchyma cell wall products, e.g. citrus fruit and sugar beets by-products, is performed in the absence of a hydroxide soaking step. This is a significant advance over the prior art as described by the Chen and Lundberg patents. Dinand, et al. (U.S. Pat. No. 5,964,983) also recommends the use of a chemical treatment step in addition to bleaching. In the present invention higher functionality (measured as viscosity) is attained compared to Dinand et al. even though less chemical treatment is used, which is likely due to the higher amount of shear and chemical energy put into the materials. The product is able to display the same or improved water retention properties and physical properties of the more strenuously refined agricultural products of the prior art, and in some cases can provide even higher water retention values, thickening and other properties that can produce unique benefits in particular fields of use.

The highly refined citrus-derived cellulose particles comprise microfibers derived from organic plant mass comprising at least 50% by weight of all fiber mass as parenchymal particle mass, the highly refined cellulose product having an alkaline water retention capacity of at least about 25 g $H_2O$/g dry highly refined cellulose particles. The highly refined cellulose particles may have a water retention capacity of at least 50 g $H_2O$/g dry highly refined cellulose product.

As used herein, the term "dry" or "dry product" refers to a mass that contains less than 15% by weight of particles as water. The organic particles mass comprises at least 50% by weight of particle mass from organic products selected from the group consisting of sugar beets, citrus fruit, grapes, tomatoes, chicory, potatoes, pineapple, apple, carrots and cranberries. A food product or food additive may have at least 0.05 percent by weight solids in the food product or food additive of the above described highly refined cellulose particles. The food product may also have at least about one percent or at least about two percent by weight of the highly refined cellulosic particles of the invention.

The term "leave-on" as used herein indicates that the compositions of this invention are intended to be applied to and allowed to remain on the skin. These leave-on compositions are to be distinguished from compositions which are applied to the skin and subsequently removed either by washing, rinsing, wiping or the like. The term "rinse-off" as used herein indicates that the compositions of the present invention are used in a context whereby the composition is ultimately rinsed or washed from the treated surface, (e.g. skin or hard surfaces) either after or during the application of the product. These rinse-off compositions are to be distinguished from compositions which are applied to the skin and allowed to remain on the skin subsequent to application.

The rinse-off compositions of this invention may be formulated into a wide variety of rinse-off compositions for personal care, including but not limited to liquid cleansers, creamy cleansers, gel cleansers, soaps and makeup removers.

The leave-on compositions of this invention may be formulated into a wide variety of leave-on compositions for personal care, including but not limited to, lotions, creams, ointments, gels, tonics, sprays, aerosols, conditioners, hand and body lotions, facial moisturizers, solid get sticks, sunscreens, anti-acne preparations, topical analgesics, mascaras, makeups, anti-perspirants and deodorants.

The topical cosmetic compositions of this invention may contain a carrier, which should be a cosmetically and/or pharmaceutically acceptable carrier. The carrier should be suitable for topical application to the skin, should have good aesthetic properties and should be compatible with other components in the composition.

These product types may comprise several types of cosmetically acceptable topical carriers including, but not limited to solutions, emulsions (e.g., microemulsions and nanoemulsions), gels, solids and liposomes. The following are non-limitative examples of such carriers. Other carriers can be formulated by those of ordinary skill in the art.

The topical compositions useful in accordance with this invention can be formulated as solutions. Solutions typically include an aqueous solvent (e.g., from about 50% to about 99.99% by weight or from about 90% to about 99% by weight of a cosmetically acceptable aqueous solvent).

Topical compositions useful in the subject invention may be formulated as a solution comprising an emollient. Such compositions preferably contain from about 2% to about 50% by weight of an emollient(s). As used herein, "emollients" refer to materials used for the prevention or relief of dryness, as well as for the protection of the skin. A wide variety of suitable emollients is known and may be used herein. Sagarin, Cosmetics, Science and Technology, 2nd Edition, Vol. 1, pp. 32-43 (1972) and the International Cosmetic Ingredient Dictionary and Handbook, eds. Wenninger and McEwen, pp. 1656-61, 1626, and 1654-55 (The Cosmetic, Toiletry, and Fragrance Assoc., Washington, D.C., $7^{th}$ Edition, 1997) (hereinafter "ICI Handbook") contains numerous examples of suitable materials.

A lotion can be made from such a solution. Lotions typically comprise from about 1% to about 20% by weight (e.g., from about 5% to about 10%) of an emollient(s) and from about 50% to about 90% by weight (e.g., from about 60% to about 80%) of water.

Another type of product that may be formulated from a solution is a cream. A cream typically comprises from about 5% to about 50% by weight (e.g., from about 10% to about 20%) of an emollient(s) and from about 45% to about 85% by weight (e.g., from about 50% to about 75%) of water.

Yet another type of product that may be formulated from a solution is an ointment. An ointment may comprise a simple base of animal or vegetable oils or semi-solid hydrocarbons. An ointment may comprise from about 2% to about 10% by weight of an emollient(s) plus from about 0.1% to about 2% by weight of a thickening agent(s). A more complete disclosure of thickening agents or viscosity increasing agents useful herein can be found in Sagarin, Cosmetics, Science and Technology, 2nd Edition, Vol. 1, pp. 72-73 (1972) and the ICI Handbook pp. 1693-1697.

The topical compositions useful in this invention formulated as emulsions. If the carrier is an emulsion, from about 1% to about 10% by weight (e.g., from about 2% to about 5%) of the carrier comprises an emulsifier(s). Emulsifiers may be nonionic, anionic or cationic. Suitable emulsifiers are disclosed in, for example, U.S. Pat. No. 3,755,560, U.S. Pat. No. 4,421,769, McCutcheon's Detergents and Emulsifiers, North American Edition, pp. 317-324 (1986), and the ICI Handbook, pp. 1673-1686.

Lotions and creams can be formulated as emulsions. Typically such lotions comprise from 0.5% to about 5% by weight of an emulsifier(s). Such creams would typically comprise from about 1% to about 20% by weight (e.g., from about 5% to about 10%) of an emollient(s); from about 20% to about 80% by weight (e.g., from 30% to about 70%) of water; and from about 1% to about 10% by weight (e.g., from about 2% to about 5%) of an emulsifier(s).

Single emulsion skin care preparations, such as lotions and creams, of the oil-in-water type and water-in-oil type are well-known in the cosmetic art and are useful in the subject invention. Multiphase emulsion compositions, such as the water-in-oil-in-water type, as disclosed in U.S. Pat. Nos. 4,254,105 and 4,960,764, are also useful in the subject invention. In general, such single or multiphase emulsions contain water, emollients, and emulsifiers as essential ingredients.

The topical compositions of this invention can also be formulated as a gel (e.g., an aqueous gel using a suitable gelling agent(s)). Suitable gelling agents for aqueous gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically comprises between about 0.1% and 5%, by weight, of such gelling agents.

The topical leave-on compositions of this invention may also be formulated as a suspension. In such a case, the compositions of this invention preferably contain a suspending agent. As used herein, the term "suspending agent" means any material known or otherwise effective in providing suspending, gelling, viscosifying, solidifying and/or thickening properties to the composition or which otherwise provide structure to the final product form. These suspending agents include gelling agents, and polymeric or nonpolymeric or inorganic thickening or viscosifying agents. Such materials will typically be solids under ambient conditions and include organic solids, silicone solids, crystalline or other gellants, inorganic particulates such as clays or silicas, or combinations thereof.

The concentration and type of suspending agent selected for use in the topical leave-on compositions of this invention will vary depending upon the desired product hardness, rheology, and/or other related product characteristics. For most suspending agents suitable for use herein, total concentrations range from about 0.1% to about 40%, more typically from about 0.1% to about 35%, by weight of the composition. Suspending agent concentrations will tend to be lower for liquid embodiments (e.g., pressurized or other liquid sprays, roll-ons, etc) and higher for semi-solid (e.g., soft solids or creams) or solid stick or cleanser embodiments. Preferably, the suspending agents are present in the compositions of this invention in an amount from about 0.1% to about 40% by weight, more preferably, the suspending agents are present in an amount from about 0.1% to about 30% by weight.

Non limiting examples of suitable suspending agents include hydrogenated castor oil (e.g., Castor wax MP80, Castor Wax, etc.), fatty alcohols (e.g., stearyl alcohol), solid paraffins, triglycerides and other similar solid suspending esters or other microcrystalline waxes, silicone and modified silicone waxes. Non limiting examples of optional suspending agents suitable for use herein are described in U.S. Pat.

No. 5,976,514 (Guskey et al.), U.S. Pat. No. 5,891,424 (Bretzler et al.), which descriptions are incorporated herein by reference.

Other suitable suspending agents include silicone elastomers at concentrations ranging from about 0.1% to about 10% by weight of the composition. Non-limiting examples of such silicone elastomer materials suitable for use as a suspending agent herein are described in U.S. Pat. No. 5,654,362 (Schulz, Jr. et al.); U.S. Pat. No. 6,060,546 (Powell et al.) and U.S. Pat. No. 5,919,437 (Lee et al.), which descriptions are incorporated herein by reference. These silicone elastomers materials can also be added for their skin feel or other cosmetic benefits alone, or for such benefits in combination with suspending agent benefits.

The topical compositions of this invention may also be formulated into a solid formulation (e.g., a wax-based stick, soap bar composition, powder, or a wipe containing powder).

The topical compositions useful in the subject invention may contain, in addition to the aforementioned components, a wide variety of additional oil-soluble materials and/or water-soluble materials conventionally used in compositions for use on skin, hair, and nails at their art-established levels.

Additional Cosmetically Active Agents

In one embodiment, the topical composition further comprises another cosmetically active agent in addition to the cellulose particles. What is meant by a "cosmetically active agent" is a compound that has a cosmetic or therapeutic effect on the skin, hair, or nails, e.g., lightening agents, darkening agents such as self-tanning agents, anti-acne agents, shine control agents, anti-microbial agents, anti-inflammatory agents, anti-mycotic agents, anti-parasite agents, external analgesics, sunscreens, photoprotectors, antioxidants, keratolytic agents, detergents/surfactants, moisturizers, nutrients, vitamins, energy enhancers, anti-perspiration agents, astringents, deodorants, hair removers, firming agents, anti-callous agents, and agents for hair, nail, and/or skin conditioning.

In one embodiment, the agent is selected from, but not limited to, hydroxy acids, benzoyl peroxide, sulfur resorcinol, ascorbic acid, D-panthenol, hydroquinone, octyl methoxycinnamate, titanium dioxide, octyl salicylate, homosalate, avobenzone, polyphenolics, carotenoids, free radical scavengers, spin traps, retinoids such as retinol and retinyl palmitate, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, peptides containing copper such as Cu:Gly-His-Lys, coenzyme Q10, peptides such as those disclosed in U.S. Pat. No. 6,620, 419, lipoic acid, amino acids such a proline and tyrosine, vitamins, lactobionic acid, acetyl-coenzyme A, niacin, riboflavin, thiamin, ribose, electron transporters such as NADH and FADH2, and other botanical extracts such as aloe vera, and derivatives and mixtures thereof. The cosmetically active agent will typically be present in the composition of the invention in an amount of from about 0.001% to about 20% by weight of the composition, e.g., about 0.01% to about 10% such as about 0.1% to about 5%.

Examples of vitamins include, but are not limited to, vitamin A, vitamin Bs such as vitamin B3, vitamin B5, and vitamin B12, vitamin C, vitamin K, and vitamin E and derivatives thereof.

Examples of hydroxy acids include, but are not limited to, glycolic acid, lactic acid, malic acid, salicylic acid, citric acid, and tartaric acid and the like.

Examples of antioxidants include, but are not limited to, water-soluble antioxidants such as sulfhydryl compounds and their derivatives (e.g., sodium metabisulfite and N-acetylcysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, and propolis. Other examples of antioxidants may be found on pages 1612-13 of the ICI Handbook.

Other Materials

Various other materials may also be present in the compositions useful in the subject invention. These include humectants, proteins and polypeptides, preservatives and an alkaline agent. Examples of such agents are disclosed in the ICI Handbook, pp. 1650-1667.

The compositions of this invention may also comprise chelating agents (e.g., EDTA) and preservatives (e.g., parabens). Examples of suitable preservatives and chelating agents are listed in pp. 1626 and 1654-55 of the ICI Handbook. In addition, the topical compositions useful herein can contain conventional cosmetic adjuvants, such as dyes, opacifiers (e.g., titanium dioxide), pigments, and fragrances.

It has been found that the linear cellulose particles useful in the compositions of this invention have excellent water and oil absorption properties. It is believed that the compositions of this invention contain hydrophobic cellulose particles may absorb sebum from the skin, thus reducing skin shininess. The compositions of this invention also are believed to protect the skin barrier by forming a hydrophobic layer on the surface of the skin and preventing the penetration of surfactants, emulsifiers or other potentially irritating ingredients. In addition, such a hydrophobic layer formed on the surface of the skin should reduce trans-epithelial water loss and increase hydration of the skin. However, in some instances, it may be desired that the cellulose particles have enhanced or decreased hydrophobic or hydrophilic properties.

Thus, the linear cellulose particles useful in the compositions of this invention may be treated with additional hydrophobic agents or hydrophilic agents, thus further enhancing hydrophobic and/or hydrophilic properties respectively, as desired. Hydrophobic agents may include but not limited to low water soluble organic compounds such as long chain fatty acids or esters such as stearic acid, oleic acid, castor oil, isododecane, silicone, and their derivatives, non-water soluble polymers, e.g. high molecular weight methylcellulose and ethylcellulose, and high molecular water insoluble fluoropolymers etc., polymerized siloxanes or polysiloxanes with the chemical formula [R2SiO]n, where R is an organic group such as methyl, ethyl, or phenyl, such as dimethicone, dimethicone copolyol, dimethicone ester; methicone and their derivatives. Hydrophilic agents such as water soluble polymers, e.g. low molecular weight methyl cellulose or hydroxypropyl methyl cellulose (PMC); sugars, e.g. monosaccharides such as fructose and glucose, disaccharides such as lactose, sucrose, or polysaccharides such as cellulose, amylose, dextran, etc. and low molecular polyvinyl alcohol, and hydrated silica may also be used to enhance the hydrophilic properties of the cellulose particles used in the compositions of this invention.

In one embodiment, linear cellulose particles may be formulated with amphiphilic cellulose particles to enhance both the water absorption and oil absorption. Examples of such amphiphilic cellulose particles include, but are not limited to, citrus particles and corn particles. The amphiphilic cellulose particles according to this invention are believed to comprise both hydrophobic and hydrophilic moieties, exhibiting both the enhanced water absorption and oil absorption properties. In particular, the amphiphilic cellulose particles many contain hydrophilic cellulosic compounds in the bulk, but also contain protein and lipids that are coated on the surface of the citrus cellulose particles to yield a hydrophobic surface property.

It also was found that the textures of the compositions formulated with the linear cellulose particles of this invention are "fluffy", silky and soft and asthetically pleasing to the touch during and after the application. The term "fluffy" as used herein refers to the bulk density of the linear cellulose particles useful in the compositions of this invention. The bulk density of the linear cellulose particles useful in the compositions of this invention is preferably from about 0.1 to about 2 (g/cm$^3$), more preferably from about 0.15 to about 1.8 g/cm$^3$, and most preferably from about 0.15 to about 1.6 g/cm$^3$. Preferably, the linear cellulose particles useful in the compositions of this invention are present in the compositions in an amount of from about 1 to about 20% by weight of the compositions, more preferably from about 1 to about 10% by weight of the compositions and most preferably in an amount of from about 1 to about 6% by weight of the compositions.

The compositions of this invention may also be formulated into and used as rinse-off skin care compositions such as cleansing compositions and scrubs and the like. Thus, in addition to the linear cellulose particles and amphiphilic cellulose particles, the rinse-off compositions of this invention preferably contain at least one cleansing agent selected from the group consisting of fatty acid soaps and synthetic surfactants and/or a mixture of such materials. Optionally, the compositions of this invention contain one or more skin conditioning agents. The compositions of this invention may also contain one or more skin therapeutic agents. Preferably, the pH of the compositions of this invention ranges from about 2 to about 11. More preferably, the pH ranges from about 3 to about 10.

The compositions of this invention may contain fatty acid soaps containing from about 6 to about 22 carbon atoms, preferably form about 8 to about 18 carbon atoms, and more preferably from about 12 to about 18 carbon atoms. Fatty acid soaps having from about 8 to about 18 carbon atoms are preferably present in the compositions of this invention in an amount of from about 1 to about 60%.

Preferably, the fatty acid soaps useful in the compositions of this invention are organic soaps obtained using organic neutralizers including, but not limited to, ammonium soap, trialkanolamine soap, aminomethyl propanol soap, aminomethyl propanedial soap and tromethamine soap, more preferably triethanolamine soap and aminomethyl propanol soap and the like.

The synthetic surfactants useful in the compositions of this invention are preferably synthetic surfactants selected from anionic, nonionic, amphoteric and zwitterionic surfactants. Preferably, they are present in the compositions of this invention in amounts from about 1 to about 40% by weight, more preferably from about 1 to about 30% and most preferably from about 5 to about 30% by weight of the composition.

Amphoteric Synthetic Surfactants

Ampholytic synthetic detergents can be broadly described as derivatives of aliphatic amines which contain a long chain of about 8 to 18 carbon atoms and an anionic water-solubilizing group, e.g., carboxy, sulfo or sulfato. Examples of compounds falling within this definition are sodium 3-dodecylaminopropionate, sodium-3-dodecylamino propane sulfonate, and dodecyl dimethylammonium hexanoate. Other examples of ampholytic and amphoteric surfactants are found in U.S. Pat. No. 3,318,817, issued to Cunningham 15 on May 9, 1967, and hereby incorporated herein by reference.

The specific preferred examples of amphoteric surfactants are those having the formula:

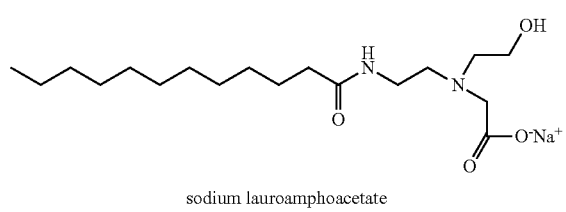

sodium lauroamphoacetate

Zwitterionic Synthetic Surfactants

Zwitterionic surface active agents are broadly described as internally neutralized derivatives of aliphatic quaternary ammonium, phosphonium and tertiary sulfonium compounds, in which the aliphatic radical can be straight chain or branched, and wherein one of the aliphatic substituents contains from about 8 to 18 carbon atoms and one contains an anionic water-solubilizing group, e.g., carboxy, sulfo, sulfato, phosphato, or phosphono. Some of these zwitterionic surfactants are described in the following U.S. Pat. Nos. 2,129,264; 2,178,353; 2,774,786; 2,813,898; and 2,828,332.

The specific preferred examples of zwitterionic surfactants are those having the formula:

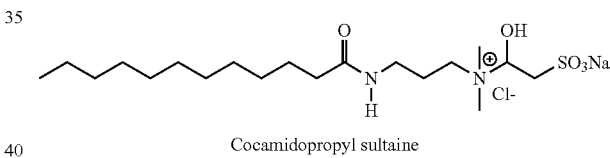

Cocamidopropyl sultaine

The water-soluble betaine surfactants are another example of a zwitterionic surfactant useful herein. These materials have the general formula:

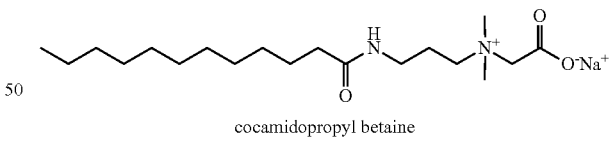

cocamidopropyl betaine

Examples of suitable betaine compounds of this type include dodecyldimethylammonium acetate, tetradecyldimethylammonium acetate, hexadecyldimethylammonium acetate, alkyldimethylammonium acetate wherein the alkyl group averages about 12 to 18 carbon atoms in length, dodecyldimethylammonium butanoate, tetradecyldimethylammonium butanoate, hexadecyldimethylammonium butanoate, dodecyldimethylammonium hexanoate, hexadecyldimethylammonium hexanoate, tetradecyldimethylammonium pentanoate and tetradecyldipropyl ammonium pentanoate. Especially preferred betaine surfactants include dodecyldimethylammonium acetate, dodecyldimethylammonium hexanoate, hexadecyldimethylammonium acetate, and hexadecyldimethylammonium hexanoate.

Polymeric Material

As used herein the term "low molecular weight" polymer refers to a polymer having a number average molecular weight ($M_n$) of about 100,000 or less as measured by gel permeation chromatography (GPC) calibrated with a poly (methyl methacrylate) (PMMA) standard. In certain preferred embodiments, low-molecular weight polymers are those having molecular weight ranges of from about 5,000 to about 80,000 $M_n$, more preferably from about 10,000 to about 50,000 $M_n$, and more preferably between about 15,000 and 40,000 $M_n$.

The polymeric material useful in the composition of this invention is preferably a polymeric material suitable for associating anionic and/or amphoteric surfactant thereto and is preferably a non-crosslinked, linear acrylic copolymer that mitigates the impaired dermal barrier damage typically associated with surfactant systems without substantially increasing viscosity build. The non-crosslinked, linear polymers are preferably of low molecular weight having a number average molecular weight of 100,000 or less as measured by gel permeation chromatography (GPC) calibrated with a poly (methyl methacrylate) (PMMA) standard (as used herein, unless otherwise specified, all number average molecular weights ($M_n$) refer to molecular weight measured in such manner). Thus, the polymeric material functions as a copolymeric mitigant. The copolymeric mitigant is polymerized from at least two monomeric components. The first monomeric component is selected from one or more $\alpha,\beta$-ethylenically unsaturated monomers containing at least one carboxylic acid group. This acid group can be derived from monoacids or diacids, anhydrides of dicarboxylic acids, monoesters of diacids, and salts thereof. The second monomeric component is hydrophobically modified (relative to the first monomeric component) and is selected from one or more $\alpha,\beta$-ethylenically unsaturated non-acid monomers containing a $C_1$ to $C_9$ alkyl group, including linear and branched $C_1$ to $C_9$ alkyl esters of (meth)acrylic acid, vinyl esters of linear and branched $C_1$ to $C_{10}$ carboxylic acids, and mixtures thereof. In one aspect of the invention the second monomeric component is represented by the formula:

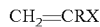

wherein R is hydrogen or methyl; X is —C(O)OR$^1$ or —OC(O)R$^2$; R$^1$ is linear or branched $C_1$ to $C_9$ alkyl; and R$^2$ is hydrogen or linear or branched $C_1$ to $C_9$ alkyl. In another aspect of the invention R$^1$ and R$^2$ is linear or branched $C_1$ to $C_8$ alkyl and in a further aspect R$^1$ and R$^2$ are linear or branched $C_2$ to $C_5$ alkyl.

Exemplary first monomeric components include (meth) acrylic acid, itaconic acid, citraconic acid, maleic acid, fumaric acid, crotonic acid, aconitic acid, and mixtures thereof. Exemplary second monomeric components include ethyl (meth)acrylate, butyl (meth)acrylate, 2-ethylhexyl (meth)acrylate, vinyl formate, vinyl acetate, 1-methylvinyl acetate, vinyl propionate, vinyl butyrate, vinyl 2-ethylhexanoate, vinyl pivalate, vinyl neodecanoate, and mixtures thereof. As used herein, the term "(meth)acrylic" acid and "(meth)acrylate" are meant to include the corresponding methyl derivatives of acrylic acid and the corresponding alkyl acrylate. For example, "(meth)acrylic" acid refers to acrylic acid and/or methacrylic acid and "(meth)acrylate" refers to alkyl acrylate and/or alkyl methacrylate.

More preferably, said first monomeric component is selected from the group consisting of (meth)acrylic acid and said second monomeric component is selected from the group consisting of at least one C1 to C9 alkyl (meth)acrylate.

The non-crosslinked, linear acrylic copolymer mitigants of the invention can be synthesized via free radical polymerization techniques known in the art. In one aspect of the invention, the amount of the first monomeric component to the second monomeric component utilized ranges from about 20:80 to about 50:50 by weight, based on the total weight of all of the monomers in the polymerization medium. In another aspect the weight ratio of the first monomeric component to the second monomeric component is about 35:65, and in a further aspect the weight ratio of first monomeric component to second monomeric component is about 25:75 all based on the total weight of all monomers in the polymerization medium.

In another aspect emulsion polymerization techniques can be used to synthesize the non-crosslinked, linear acrylic copolymer mitigants that may be useful in the invention. In a typical emulsion polymerization, a mixture of the disclosed monomers is added with mixing agitation to a solution of emulsifying surfactant, such as, for example, an anionic surfactant (e.g., fatty alcohol sulfates or alkyl sulfonates), in a suitable amount of water, in a suitable reactor, to prepare a monomer emulsion. The emulsion is deoxygenated by any convenient method, such as by sparging with nitrogen, and then a polymerization reaction is initiated by adding a polymerization catalyst (initiator) such as sodium persulfate, or any other suitable addition polymerization catalyst, as is well known in the emulsion polymerization art. The polymerization medium is agitated until the polymerization is complete, typically for a time in the range of about 4 to about 16 hours. The monomer emulsion can be heated to a temperature in the range of about 70 to about 95° C. prior to addition of the initiator, if desired. Unreacted monomer can be eliminated by addition of more catalyst, as is well known in the emulsion polymerization art. The resulting polymer emulsion product can then be discharged from the reactor and packaged for storage or use. Optionally, the pH or other physical and chemical characteristics of the emulsion can be adjusted prior to discharge from the reactor. Typically, the product emulsion has a total solids content in the range of about 10 to about 50% by weight. Typically, the total polymer content (polymer solids) of the product emulsion is in the range of about 15 to about 45% by weight, generally not more than about 35% by weight.

In one aspect, the number average molecular weight ($M_n$) of the linear copolymeric mitigants that may be useful in this invention as measured by gel permeation chromatography (GPC) calibrated with a poly(methyl methacrylate) (PMMA) standard is 100,000 or less. In another aspect of the invention, the molecular weight ranges between about 5,000 and about 80,000$M_n$, in a further aspect between about 10,000 and 50,000 $M_n$, and in a still further aspect between about 15,000 and 40,000 $M_n$.

In one aspect of the invention, the linear copolymeric mitigants have a viscosity of 500 mPa·s or less (Brookfield RVT, 20 rpm, spindle no. 1) at a 5% by weight polymer solids concentration in deionized water and neutralized to pH 7 with an 18% by weight NaOH solution. The viscosity can range from about 1 to about 500 mPa·s in another aspect, from about 10 to about 250 mPa·s in a further aspect, and from about 15 to about 150 mPa·s in a still further aspect.

Preferably, the low molecular weight, non-crosslinked linear acrylic copolymer is potassium acrylates copolymer.

Any of a variety of non-ethoxylated anionic surfactants may be combined with a polymeric material of this invention to form a cleansing composition according to preferred embodiments of the present invention. Non-ethoxylated anionic surfactants are surfactants that have a negative charge and do not contain any ethoxylated segments, that is to say there are no —(C—C—O)$_v$— segments on the surfactants. According to certain embodiments, suitable non-ethoxylated anionic surfactants include those selected from the following classes of surfactants: alkyl sulfates, alkyl sulfonates, alkyl monoglyceride sulfonates, alkylaryl sulfonates, alkyl sulfosuccinates, alkyl sulfosuccinamates, alkyl carboxylates, fatty alkyl sulfoacetates, alkyl phosphates, acylglutamates, sarcosinates, taurates, and mixtures of two or more thereof. Examples of certain preferred anionic surfactants include:

Alkyl Sulfates of the Formula

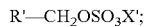

R'—CH$_2$OSO$_3$X';

Alkyl Monoglyceride Sulfates of the Formula

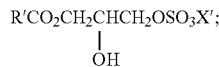

R'CO$_2$CH$_2$CHCH$_2$OSO$_3$X';
|
OH

Alkyl Monoglyceride Sulfonates of the Formula

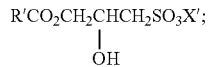

R'CO$_2$CH$_2$CHCH$_2$SO$_3$X';
|
OH

Alkyl Sulfonates of the Formula

R'—SO$_3$X';

Alkylaryl Sulfonates of the Formula

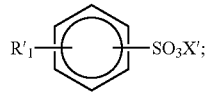

Alkyl Sulfosuccinates of the Formula:

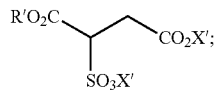

Alkyl Phosphates
wherein
R' is an alkyl group having from about 7 to about 22, and preferably from about 7 to about 16 carbon atoms,
R'$_1$ is an alkyl group having from about 1 to about 18, and preferably from about 8 to about 14 carbon atoms,
R'$_2$ is a substituent of a natural or synthetic I-amino acid,
X' is selected from the group consisting of alkali metal ions, alkaline earth metal ions, ammonium ions, and ammonium ions substituted with from about 1 to about 3 substituents, each of the substituents may be the same or different and are selected from the group consisting of alkyl groups having from 1 to 4 carbon atoms and hydroxyalkyl groups having from about 2 to about 4 carbon atoms and
w is an integer from 0 to 20;
and mixtures thereof.

According to certain embodiments set forth in patent application U.S. Ser. Nos. 12/822,329 and 12/976,573, the anionic surfactant of this invention is preferably a non-ethoxylated SO$_x$ anionic surfactant conforming to the structure below

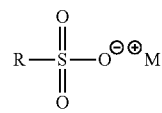

Where SO$_3^-$ is the anionic hydrophilic group, M$^+$ is a monovalent cation (such as NH$_4^+$, Na$^+$, K$^+$, (HOCH$_2$CH$_2$)$_3$N$^+$, etc.), and R comprises any of a broad range of hydrophobic groups and optionally, a) functional groups to link the hydrophilic and hydrophobic moieties and/or b) additional hydrophilic groups. Examples include:

Alkyl sulfonates, where R equals $C_6$-$C_{20}$ alkyl, (linear or branched, saturated or unsaturated), preferably $C_{10}$-$C_{18-}$, and most preferably $C_{12}$-$C_{17}$. Specific examples include Sodium $C_{13}$-$C_{17}$ Alkane Sulfonate (R=$C_{13}$-$C_{17}$ alkyl, M$^+$=Na$^+$) and Sodium $C_{14}$-$C_{17}$ Alkyl Sec Sulfonate (R=s-$C_{13}$-$C_{17}$ alkyl, M$^+$=Na$^+$)

Alpha olefin sulfonates, where R equals a mixture of

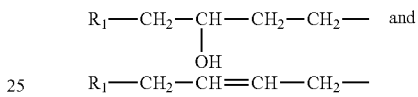

where $R_1$=$C_4$-$C_{16}$ alkyl or mixtures thereof, preferably $C_6$-$C_{12}$, more preferably $C_8$-$C_{12}$, and most preferably $C_{10}$-$C_{12}$. Specific examples include Sodium $C_{12-14}$ Olefin Sulfonate (R$_1$=$C_8$-$C_{10}$ alkyl, M$^+$=Na$^+$) and Sodium $C_{14-16}$ Olefin Sulfonate (R$_1$=$C_{10}$-$C_{12}$ alkyl, M$^+$=Na$^+$).

Alkyl sulfate esters, where $R_1$=$C_6$-$C_{20}$, $R_1$—O—

(linear or branched, saturated or unsaturated), preferably $C_{12}$-$C_{18}$, more preferably $C_{12}$-$C_{16}$, and most preferably $C_{12}$-$C_{14}$. Specific examples include Ammonium Lauryl Sulfate (R$_1$=lauryl, $C_{12}H_{25}$, M$^+$=NH$_4^+$), Sodium Lauryl Sulfate (R$_1$=lauryl, $C_{12}H_{25}$, M$^+$=Na$^+$), and Sodium Cocosulfate (R$_1$=coco alkyl, M$^+$=Na$^+$).

As used herein, the term "amphoteric" means: 1) molecules that contain both acidic and basic sites such as, for example, an amino acid containing both amino (basic) and acid (e.g., carboxylic acid, acidic) functional groups; or 2) zwitterionic molecules which possess both positive and negative charges within the same molecule. The charges of the latter may be either dependent on or independent of the pH of the composition. Examples of zwitterionic materials include, but are not limited to, alkyl betaines and amidoalkyl betaines as set forth above and below. The amphoteric surfactants are disclosed herein without a counter ion. One skilled in the art would readily recognize that under the pH conditions of the compositions of this invention, the amphoteric surfactants are either electrically neutral by virtue of having balancing positive and negative charges, or they have counter ions such as alkali metal, alkaline earth, or ammonium counter ions.

Examples of amphoteric surfactants suitable for use in this invention include, but are not limited to, amphocarboxylates such as alkylamphoacetates (mono or di); alkyl betaines; amidoalkyl betaines; alkyl sultaines; amidoalkyl sultaines; amphophosphates; phosphorylated imidazolines such as phosphobetaines and pyrophosphobetaines; carboxyalkyl alkyl polyamines; alkylimino-dipropionates; alkylamphoglycinates (mono or di); alkylamphoproprionates (mono or di),); N-alkyl β-aminoproprionic acids; alkylpolyamino carboxylates; and mixtures thereof.

Examples of suitable amphocarboxylate compounds include those of the formula:

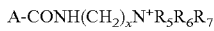

wherein
A is an alkyl or alkenyl group having from about 7 to about 21, e.g. from about 10 to about 16 carbon atoms;
x is an integer of from about 2 to about 6;
$R_5$ is hydrogen or a carboxyalkyl group containing from about 2 to about 3 carbon atoms;
$R_6$ is a hydroxyalkyl group containing from about 2 to about 3 carbon atoms or is a group of the formula:

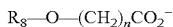

wherein
$R_8$ is an alkylene group having from about 2 to about 3 carbon atoms and n is 1 or 2; and
$R_7$ is a carboxyalkyl group containing from about 2 to about 3 carbon atoms;
Examples of suitable alkyl betaines include those compounds of the formula:

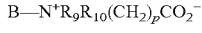

wherein
B is an alkyl or alkenyl group having from about 8 to about 22, e.g., from about 8 to about 16 carbon atoms;
$R_9$ and $R_{10}$ are each independently an alkyl or hydroxyalkyl group having from about 1 to about 4 carbon atoms; and
p is 1 or 2.
A preferred betaine for use in this invention is lauryl betaine, available commercially from Albright & Wilson, Ltd. of West Midlands, United Kingdom as "Empigen BB/J."
Examples of suitable amidoalkyl betaines include those compounds of the formula:

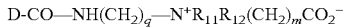

wherein
D is an alkyl or alkenyl group having from about 7 to about 21, e.g. from about 7 to about 15 carbon atoms;
$R_{11}$ and $R_{12}$ are each independently an alkyl or
Hydroxyalkyl group having from about 1 to about 4 carbon atoms;
q is an integer from about 2 to about 6; and m is 1 or 2.
One amidoalkyl betaine is cocamidopropyl betaine, available commercially from Goldschmidt Chemical Corporation of Hopewell, Va. under the tradename, "Tegobetaine L7."
Examples of suitable amidoalkyl sultaines include those compounds of the formula

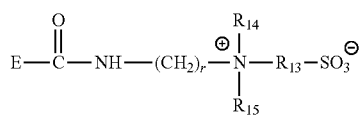

wherein
E is an alkyl or alkenyl group having from about 7 to about 21, e.g. from about 7 to about 15 carbon atoms;
$R_{14}$ and $R_{15}$ are each independently an alkyl, or hydroxyalkyl group having from about 1 to about 4 carbon atoms;
r is an integer from about 2 to about 6; and
$R_{13}$ is an alkylene or hydroxyalkylene group having from about 2 to about 3 carbon atoms;

In one embodiment, the amidoalkyl sultaine is cocamidopropyl hydroxysultaine, available commercially from Rhone-Poulenc Inc. of Cranbury, N.J. under the tradename, "Mirataine CBS."
Examples of suitable amphophosphate compounds include those of the formula:

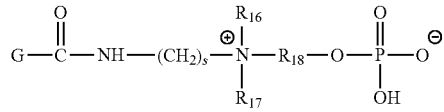

wherein
G is an alkyl or alkenyl group having about 7 to about 21, e.g. from about 7 to about 15 carbon atoms;
s is an integer from about 2 to about 6;
$R_{16}$ is hydrogen or a carboxyalkyl group containing from about 2 to about 3 carbon atoms;
$R_{17}$ is a hydroxyalkyl group containing from about 2 to about 3 carbon atoms or a group of the formula:

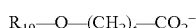

wherein $R_{19}$ is an alkylene or hydroxyalkylene group having from about 2 to about 3 carbon atoms and t is 1 or 2; and
$R_{18}$ is an alkylene or hydroxyalkylene group having from about 2 to about 3 carbon atoms.
In one embodiment, the amphophosphate compounds are sodium lauroampho PG-acetate phosphate, available commercially from Mona Industries of Paterson, N.J. under the tradename, "Monateric 1023," and those disclosed in U.S. Pat. No. 4,380,637, which is incorporated herein by reference.
Examples of suitable phosphobetaines include those compounds of the formula:

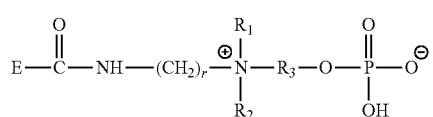

wherein E, r, $R_1$, $R_2$ and $R_3$, are as defined above. In one embodiment, the phosphobetaine compounds are those disclosed in U.S. Pat. Nos. 4,215,064, 4,617,414, and 4,233,192, which are all incorporated herein by reference.
Examples of suitable pyrophosphobetaines include those compounds of the formula:

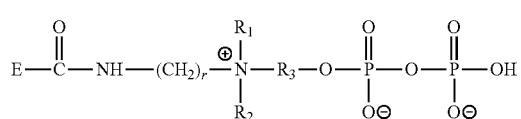

wherein E, r, $R_1$, $R_2$ and $R_3$, are as defined above. In one embodiment, the pyrophosphobetaine compounds are those disclosed in U.S. Pat. Nos. 4,382,036, 4,372,869, and 4,617,414, which are all incorporated herein by reference.
Examples of suitable carboxyalkyl alkylpolyamines include those of the formula:

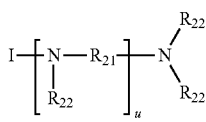

wherein

I is an alkyl or alkenyl group containing from about 8 to about 22, e.g. from about 8 to about 16 carbon atoms;

$R_{22}$ is a carboxyalkyl group having from about 2 to about 3 carbon atoms;

$R_{21}$ is an alkylene group having from about 2 to about 3 carbon atoms and u is an integer from about 1 to about 4.

The cleansing compositions produced, as well as any of the compositions containing polymeric material and a surfactant component having at least one non-ethoxylated anionic surfactant and at least one amphoteric surfactant that are combined in the combining step according to the methods of this invention may further contain any of a variety of other components nonexclusively including additives which enhance the appearance, feel and fragrance of the compositions, such as colorants, fragrances, preservatives, pH adjusting agents and the like.

Any of a variety of nonionic surfactants are suitable for use in the compositions of this invention, keeping in mind that total surfactant load should not exceed about 14 weight percent of the compositions set forth herein. Examples of suitable nonionic surfactants include, but are not limited to, fatty alcohol acid or amide ethoxylates, monoglyceride ethoxylates, sorbitan ester ethoxylates, alkyl polyglucosides, polyglyceryl esters, mixtures thereof, and the like. Certain preferred nonionic surfactants include alkyl polyglucosides, such as but not limited to coco-glucoside and decyl-glucoside, and polyglyceryl esters, such as but not limited to polyglyceryl-10 laurate and polyglyceryl-10 oleate.

Any of a variety of commercially available secondary conditioners, such as volatile silicones, which impart additional attributes, such as gloss to the hair are suitable for use in this invention. In one embodiment, the volatile silicone conditioning agent has an atmospheric pressure boiling point less than about 220° C. The volatile silicone conditioner may be present in an amount of from about 0 percent to about 3 percent, e.g. from about 0.25 percent to about 2.5 percent or from about 0.5 percent to about 1 percent, based on the overall weight of the composition. Examples of suitable volatile silicones nonexclusively include polydimethylsiloxane, polydimethylcyclosiloxane, hexamethyldisiloxane, cyclomethicone fluids such as polydimethylcyclosiloxane available commercially from Dow Corning Corporation of Midland, Mich. under the tradename, "DC-345" and mixtures thereof, and preferably include cyclomethicone fluids.

Any of a variety of commercially available humectants, which are capable of providing moisturizing and conditioning properties to the personal cleansing composition, are suitable for use in this invention. The humectant may be present in an amount of from about 0 percent to about 10 percent, e.g. from about 0.5 percent to about 5 percent or from about 0.5 percent to about 3 percent, based on the overall weight of the composition. Examples of suitable humectants nonexclusively include: 1) water soluble liquid polyols selected from the group comprising glycerine, propylene glycol, hexylene glycol, butylene glycol, dipropylene glycol, and mixtures thereof; 2) polyalkylene glycol of the formula: $HO-(R''O)_b-H$, wherein R" is an alkylene group having from about 2 to about 3 carbon atoms and b is an integer of from about 2 to about 10; 3) polyethylene glycol ether of methyl glucose of formula $CH_3-C_6H_{10}O_5-(OCH_2CH_2)_c-OH$, wherein c is an integer from about 5 to about 25; 4) urea; and 5) mixtures thereof, with glycerine being the preferred humectant.

Examples of suitable chelating agents include those which are capable of protecting and preserving the compositions of this invention. Preferably, the chelating agent is ethylenediamine tetracetic acid ("EDTA"), and more preferably is tetrasodium EDTA, available commercially from Dow Chemical Company of Midland, Mich. under the tradename, "Versene 100XL" and is present in an amount, based upon the total weight of the composition, from about 0 to about 0.5 percent or from about 0.05 percent to about 0.25 percent.

Suitable preservatives include organic acid preservatives may include benzoic acid and alkali metal and ammonium salts thereof (e.g. sodium benzoate), sorbic acid and alkali metal and ammonium salts thereof (e.g. potassium sorbate), p-Anisic acid and alkali metal and ammonium salts thereof, and salicylic acid and alkali metal and ammonium salts thereof. The pH of the composition may be adjusted to the appropriate acidic value using any cosmetically acceptable organic or inorganic acid, such as citric acid, acetic acid, glycolic acid, lactic acid, malic acid, tartaric acid, or hydrochloric acid.

In one embodiment of the composition, sodium benzoate is present in the composition in an amount, based upon the total weight of the composition, from about 0 to about 0.5 percent. In another embodiment, potassium sorbate is present in the composition in an amount, based upon the total weight of the composition, from about 0 to about 0.6 percent, more preferably from about 0.3 to about 0.5 percent.

The methods of this invention may further comprise any of a variety of steps for mixing or introducing one or more of the optional components described hereinabove with or into a composition comprising a polymeric material before, after, or simultaneously with the combining step described above. While in certain embodiments, the order of mixing is not critical, it is preferable, in other embodiments, to pre-blend certain components, such as the fragrance and the nonionic surfactant before adding such components into a composition comprising a polymeric material and/or an anionic surfactant.

The cleansing methods of this invention may further include any of a variety of additional, optional steps associated conventionally with cleansing hair and skin including, for example, lathering, rinsing steps, and the like.

The foregoing information regarding low molecular weight hydrophobically-modified polymers as well as compositions that may be useful in the methods of this invention are set forth in U.S. Pat. No. 7,803,403, US2006/0257348, and US20070111910, all of which are hereby incorporated herein by reference.

The methods and compositions of this invention illustratively disclosed herein suitably may be practiced in the absence of any component, ingredient, or step which is not specifically disclosed herein. Several examples are set forth below to further illustrate the nature of the invention and the manner of carrying it out. However, the invention should not be considered as being limited to the details thereof.

The topical compositions useful in the compositions of this invention may be formulated as solutions. Solutions typically include an aqueous solvent (e.g., from about 50% to about 99.99% or from about 90% to about 99% of a cosmetically acceptable aqueous solvent).

Topical compositions useful in the subject invention may be formulated as a solution comprising an emollient. Such compositions preferably contain from about 2% to about 50% by weight of an emollient(s). As used herein, "emollients" refer to materials used for the prevention or relief of dryness, as well as for the protection of the skin. A wide variety of suitable emollients is known and may be used herein. Sagarin, Cosmetics, Science and Technology, 2nd Edition, Vol. 1, pp. 32-43 (1972) and the International Cosmetic Ingredient Dictionary and Handbook, eds. Wenninger and McEwen, pp. 1656-61, 1626, and 1654-55 (The Cosmetic, Toiletry, and Fragrance Assoc., Washington, D.C., 7$^{th}$ Edition, 1997) (hereinafter "ICI Handbook") contains numerous examples of suitable materials.

Preferably, the rinse-off compositions of this invention contain from about 1% to about 20% by weight (e.g., from about 5% to about 10%) of an emollient(s) and from about 50% to about 90% (e.g., from about 60% to about 80%) of water. Topical compositions useful in the subject invention may be formulated as a solution containing an emulsifier. Such compositions preferably contain from about 0.1% to about 1% by weight of an emulsifier. Emulsifiers may be nonionic, anionic or cationic. Suitable emulsifiers are disclosed in, for example, U.S. Pat. No. 3,755,560, U.S. Pat. No. 4,421,769, McCutcheon's Detergents and Emulsifiers, North American Edition, pp. 317-324 (1986), and the ICI Handbook, pp. 1673-1686.

Another type of product that may be formulated from a solution is a creamy cleanser. A creamy cleanser preferably contains from about 5% to about 50% by weight (e.g., from about 10% to about 20%) of an emollient(s) and from about 45% to about 85% by weight (e.g., from about 50% to about 75%) of water. The topical compositions useful in this invention formulated as emulsions. If the carrier is an emulsion, from about 1% to about 10% by weight (e.g., from about 2% to about 5%) of the carrier comprises an emulsifier(s). Emulsifiers may be nonionic, anionic or cationic. Suitable emulsifiers are disclosed in, for example, U.S. Pat. No. 3,755,560, U.S. Pat. No. 4,421,769, McCutcheon's Detergents and Emulsifiers, North American Edition, pp. 317-324 (1986), and the ICI Handbook, pp. 1673-1686.

The compositions of this invention preferably contain linear cellulose particles and amphiphilic linear cellulose particles in a ratio of from about 1:10 to about 10:1. More preferably, they should be present in an amount of from about 1:9 to about 9:1. Most preferably, the amount of amphiphilic linear cellulose particles should be present in an amount of about 10% by weight of the sum total of amphiphilic linear cellulose particles and linear cellulose particles.

Methods of Cleansing and Conditioning the Skin or Hair

The methods of this invention also relate to methods of cleansing and conditioning the skin or hair with a personal cleansing product of the present invention. These methods comprise, the steps of wetting with water a substantially dry, disposable, single use personal cleansing product comprising a water insoluble substrate, a lathering surfactant, and a conditioning component, and contacting the skin or hair with said wetted product. In further embodiments, the methods and compositions of this invention are also useful for delivering various active ingredients to the skin or hair.

The compositions of this invention may be substantially dry and may be wetted with water prior to use. The product may be wetted by immersion in a container filled with water or by placing it under a stream of water. Lather may be generated from the product by mechanically agitating and/or deforming the product either prior to or during contact of the product with the skin or hair. The resulting lather is useful for cleansing and conditioning the skin or hair. During the cleansing process and subsequent rinsing with water, the conditioning agents and active ingredients are deposited onto the skin or hair. Deposition of conditioning agents and active ingredients are enhanced by the physical contact of the substrate with the skin or hair.

The invention will be further described by reference to the following examples in order to further illustrate the present invention and advantages thereof. These examples are not meant to be limiting but illustrative.

The compounds are indicated, depending on the case, as their CTFA name or their chemical name, and the percentages are given on a weight basis, except where otherwise mentioned.

Example 1

Characterization of Hydrophobic and Hydrophilic Linear Cellulose Particles

Hydrophobic cotton particles and Hydrophilic Cotton particles listed in Table 1 below were characterized as followed:
Materials:

TABLE 1

| Materials | |
|---|---|
| Squalene | |
| DI Water | |
| Hydrophobic Linear Cotton Particles (available from Goonvean of Cornwall England) | Hydrophobic Cotton Particle #1 |
| Hydrophobic Linear Cotton Particles (available from IFC of North Tonawanda, NY) | Hydrophobic Cotton Particle #2 |
| Hydrophilic Cotton Particles (available from Resources of Nature of South Plainfield, NJ) | Hydrophilic Cotton Particle #1 |
| Citrus Particless (available from Fiberstar Sales of River Falls, WI) | Citrus Particle |

Example 1A

Particle Size Measurement

The particle size of the cellulose materials was determined by Mie/Fraunhofer Laser Scattering method using a Malvern Hydro 2000S Particle Size Analyzer by the following procedure:

1. Ensured the cell windows and lenses are clean and free from scratches.
2. Flushed (using de-ionized water) and drained the accessory at least 2 times in order to eliminate any contamination from previous samples.
3. Turned off the pump/stirrer and turned on the ultrasonics for 30 seconds to allow for air bubbles to dissipate.
4. Filled the dispersion unit with DI water. Adjusted the pump/stirrer speed to 2100 rpm, and then turned off the pump for about 3 seconds to allow the air to dissipate.

Then slowly turned the pump back on to 2100 rpm. Toped up the water in the dispersion unit to replace the volume of air displaced.

5. Added 4 drops of 5% IGEPAL CA 630 (non ionic detergent) in the tank and allow dispersing before measuring the background. If this concentration causes bubble formation, cleaned the unit and repeat the procedure using 2 drops of surfactant. To ensure the background give a clean value. Follow the 2-150 and 20-20 rule (First two detectors should have light intensity less than 150 units and the detector number 20 should have light intensity less than 20 units)
6. When the system was clean, added diluted sample to be measured in the dispersion unit in an amount of about 2 mg in 10 grams water.
7. When the obscuration caused by the particles in the sample is 2 to 5%, start the measurement. Note D50 and D90 in microns. (D50 refers to 50% of the particles are less than the value; D90 refers to 50% of the particles are less than the value)
8. The experiment was repeated three times and the average of the three results was recorded as the final value.

The average particle size of various cellulose particles outlined in Table 1 was determined and shown in Table 2.

TABLE 2

|  | Particle Size D90 (microns) | Particle Size D80 (microns) | Particle Size D50 (microns) |
| --- | --- | --- | --- |
| Hydrophilic Cotton Particles | 170 | 125 | 70 |
| Hydrophobic Linear Cotton Particles (#1) | 500 | 200 | 55 |
| Hydrophobic Linear Cotton Particles (#2) | 270 | 125 | 50 |
| Citrus Particles | 200 | 140 | 75 |

Example 1B

Contact Angle

The contact angles of various cellulose particles outlined in Table 1 were determined as follows:

40 Grams of the cotton particles and citrus particles shown in Table 1 were placed in a particle sample holder; the surface was compressed with a consistent force to create a smooth and compact surface of the particles. 500 µl micro syringe filled with test liquid (water), 0.52 mm needle was used to dispense and deposit 5 µl droplets on the surface. Contact Angles of the droplet on each of the cotton and citrus particle samples were measured and calculated with Video-based DataPhysics optical contact angle measuring system OCA 20 with software SCA20 from three replicate tests on each sample, results are shown in Table 3.

TABLE 3

| Material | Initial Water Contact Angle (degrees) |
| --- | --- |
| Hydrophobic Linear Cotton Particles (#2) | 136.2 (5.8)* |

TABLE 3-continued

| Material | Initial Water Contact Angle (degrees) |
| --- | --- |
| Hydrophilic Cotton Particles | 39.1 (4)* |
| Hydrophobic Linear Cotton Particles (#1) | 122.3 (3.2)* |
| Amphiphilic Citrus Particles | 117.9 (12.6) |

*represents standard deviation

As shown in Table 3, hydrophobic cotton particles and citrus particles exhibited a larger water contact angle compared to the hydrophilic cotton particles. Citrus particles also exhibited an interaction of particles climbing the water droplets.

Example 1C

Infrared Spectra

Figure 2:
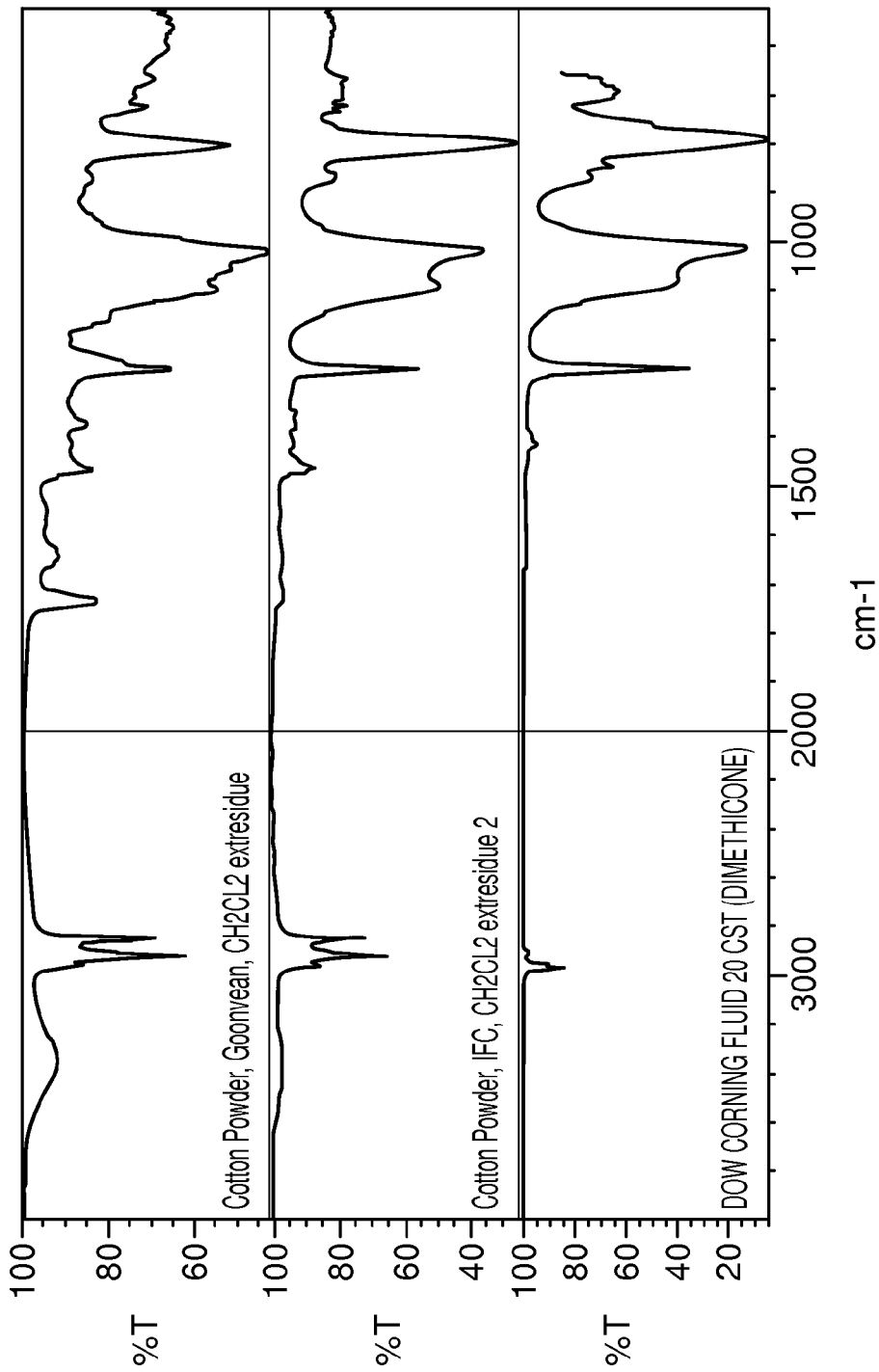
FIG. 2 is a graph of Infrared spectra of various solvent extracts from hydrophobic cotton powder and dimethicone.

Infrared spectrum analysis was performed on three cotton particles as follows:

Solvent extraction of the cotton materials using methylene chloride was conducted and followed by IR analysis of the evaporated residues and forth in FIGS. 1 and 2 hereto.

The spectra (shown in FIGS. 1 and 2) showed extract residues from the two hydrophobic linear cotton particles (#2 and #1) along with a dimethicone reference spectrum.

Solvent extractions of the two hydrophobic cotton materials (IFC and Goonvean) showed a significant amount of waxy semi-solid residue, and relatively little from the hydrophilic cotton materials. It is believed that this waxy semi-solid residue coating is responsible for the hydrophobic nature of these two hydrophobic cotton particles.

Infrared analysis of the #2 and #1 hydrophobic cotton residues shows them both to contain silicone (dimethicone or related polymer) along with other components. The #2 residue includes a long chain hydrocarbon wax-like material (as indicated by split peaks around 1375 and 725 cm-1) while the #1 residue includes an ester component (as indicated by IR peaks around 1735 and 1250 cm-1).

The hydrophilic cotton particles (Virgin Cotton Flock) showed negligible extractable residue. The morphology of this material was significantly different from the other two materials indicating a higher degree of processing, reducing much of the cotton particle into a fine powdery material. The hydrophilic nature of this material is likely due to the inherent absorbent properties of cotton, and the lack of a repellant finish treatment.

Further, Infrared analysis showed that all three cotton materials are typical "cellulosic" materials. Characterization of the three different cotton materials showed the hydrophobic (#2 and #1) being composed of a silicone based hydrophobic treatment. In contrast, the hydrophilic cotton lacks of the silicone based hydrophobic repellant treatment.

Example 2

Specific Surface Area

Inverse Gas Chromatography (IGC) has been reported in various papers as a good method to determine isotherms at finite concentration and ambient temperatures, using organic probe molecules. (Thielmann, F., Burnett, D. J. and Heng, J. Y. Y. (2007) Determination of the surface energy distributions of different processed lactose. *Drug Dev. Ind. Pharm.* 33, 1240-1253. And see also Yla-Maihaniemi, P. P. et al. (2008) Inverse gas chromatographic method for measuring the dispersive surface energy distribution for particulates. Langmuir, 24, p. 9551-9557.

Specific surface area was determined with IGC using octane by measuring the octane adsorption isotherms at 30° C. and 0% RH. The results of these determinations are shown in Table 4. "BET" is a measurement of specific surface area known to those of ordinary skill in the art.

TABLE 4

Specific surface areas of Particles (BET/IGC)

| Sample | Surface area ($m^2/gr.$) |
|---|---|
| Hydrophilic Cotton Particles | 1.4 |
| Hydrophobic Linear Cotton Particles (#1) | 1.23 |
| Hydrophobic Linear Cotton Particles (#2) | 1.6 |
| Amphiphilic Citrus Particles | 3.2 |

Example 3

Absorption Capacity and Retention

The absorption capacity of olive oil by the dry cotton particles in Table 1 was measured in standard conditions (i.e. ambient temperature and pressure). The saturated particles were also subjected to centrifugal force to measure their retention power.

When porous media containing liquid is subjected to a force, the liquid is gradually evacuated from large pores then from increasingly small pores as pressure increases. Media containing a high pore volume distribution of smaller pores (or effective pores) can retain more liquid under higher constraint and this retentive power may be a useful feature when the desired role of the media is to retain a liquid (sponge effect).

In order to evaluate the retentive power of the particles, over-saturated oil/particles combinations were subjected to centrifugal force (8000 rpm, 300 seconds) and remaining oil was measured. The results of this measurement are shown in Table 5.

After acceleration, the remaining oil can be expressed as a proportion of the amount of the saturating oil (=mass of oil remaining/mass of oil initially in the blend) or else one can express the amount of oil remaining as a mass fraction of the particles/oil mix (=mass of oil remaining/mass of the powder/oil complex). Both calculations may provide different insights and are expressed in the following table.

TABLE 5

Absorption Capacity and Retention of glyceryl trioleate (olive oil) on Cotton Particles.

| Sample | Absorption capacity of olive oil (% w/w) | Retention @ 8000 rpm (% of saturation) | Retention @ 8000 rpm (% of blend) |
|---|---|---|---|
| Hydrophilic Cotton Particles | 130 | 14 | 16 |
| Hydrophobic Linear Cotton Particles (#1) | 445 | 14 | 38 |
| Hydrophobic Linear Cotton Particles (#2) | 322 | 7 | 18 |
| Amphiphilic Citrus Particles | 58 | 62 | 25 |

Two Hydrophobic Linear Cotton particles (#1 and #2) demonstrated very high absorption of oil in the dry, loosely packed state. Further, the Hydrophobic Linear Cotton Particles (#1) retained a high amount of triglyceride even under applied acceleration (and retaining more than the Hydrophilic Cotton Particles and Amphiphilic Citrus Particles had initially absorbed).

Although Amphiphilic Citrus Particles retained the highest proportion of what it had absorbed (due to high specific surface area, higher density which created a larger number of small interstitial spaces), it was hindered by a smaller initial absorption, which is probably a consequence of the smaller available volume in the particle's free space.

Example 4

Speed of Oil Absorption

The speed of oil absorption by a material may be determined by procedures as follows:

A template of a 6×4 cm rectangle was cut from a 0.25 mm thick paper. With a 4×2 cm rectangle window cut in the middle with 1 cm of paper around the edge of the window. A glass microscope slide was weighed and its mass recorded. The template was placed on the slide and the test material dispensed in the window of the template. The material was spread across the window with a metal spatula to create an even rectangular layer with a mass of ~0.24 g (±0.01 g). The template was carefully removed, edges of the slide cleaned off with a spatula or gloved fingertip as necessary, and the mass of the slide+material recorded. The slide (with oil-absorbing particles layer) was placed flat in an incubator at 32° C. 0.0858 g of the sebum component of interest was dispensed via 0-100 µL pipette (liquids) to the slide at one side of and in contact with the particle layer. (For squalene, 100 µL was used; for triolein, 94.3 µL was used based on suppliers' stated densities). The slide was left undisturbed in the incubator for 15 seconds for follow-up test), with a timer started just as the drop was dispensed. After 15 seconds, the slide was removed from the incubator and any unabsorbed sebum component was carefully wiped from the slide using a Kimwipe. The slide was weighed to determine the amount of the sebum component absorbed by the powder during the absorbance period. The Steps above were repeated for each slide, with each sebum component/powder combination tested at least in triplicate. Ratios were calculated to show the mass of sebum component absorbed per mass of oil-absorbing powder within 15 seconds. The results of this determination are set forth in FIG. 3 hereto.

Figure 3:
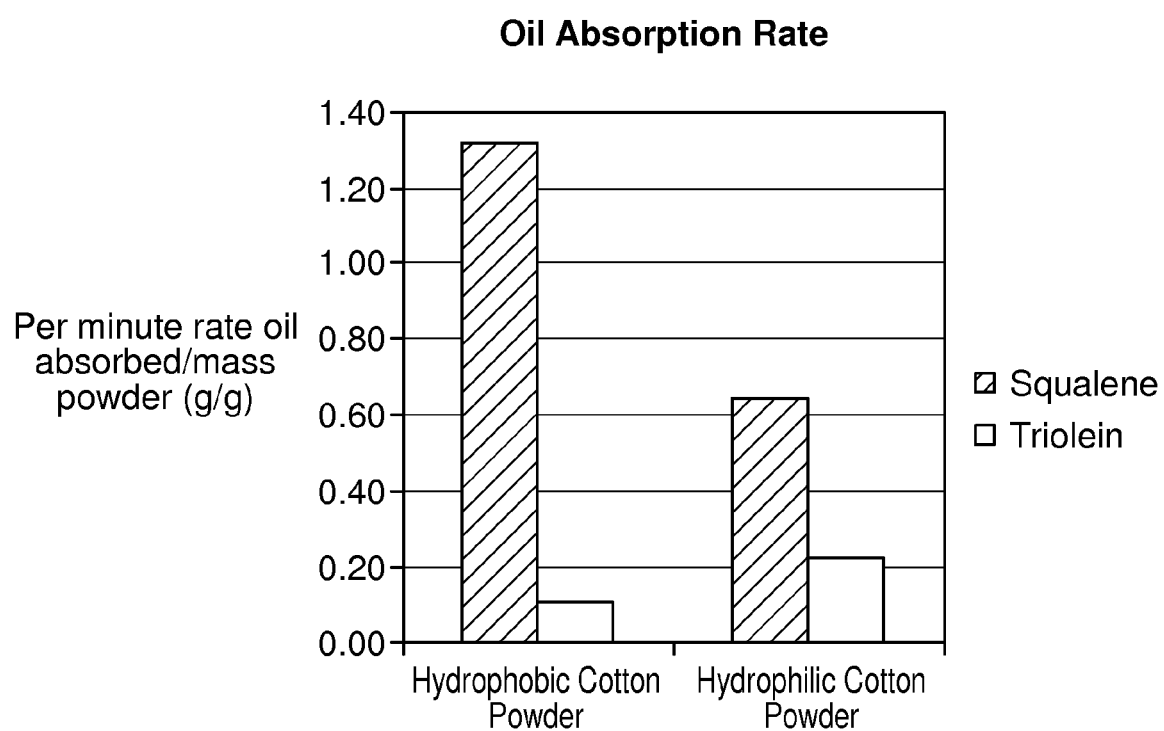
FIG. 3 is a graph illustrating oil absorption rates of hydrophilic and hydrophobic cotton powder.

FIG. 3 demonstrates that cotton powder (#1 hydrophobic cotton powder) absorbs both squalene and triglyceride much faster than virgin cotton powder.

Example 5

Speed of Water Absorption

The speed of water absorption of materials was determined by the procedure set forth as follows:

A gravimetric absorption test (GAT) Method was used to determine the water absorption kinetics of hydrophobic cotton powder vs. hydrophilic cotton powder. The cotton powder sample was loaded into a small cylinder container, and the water was introduced in contact with the cotton powder through a water reservoir on a scale, the change in water weight arising from water transfer or absorption by cotton powder was recorded electronically by a computer over the study duration. The absorption rate was calculated and plotted for different cotton powder samples.

Figure 4:
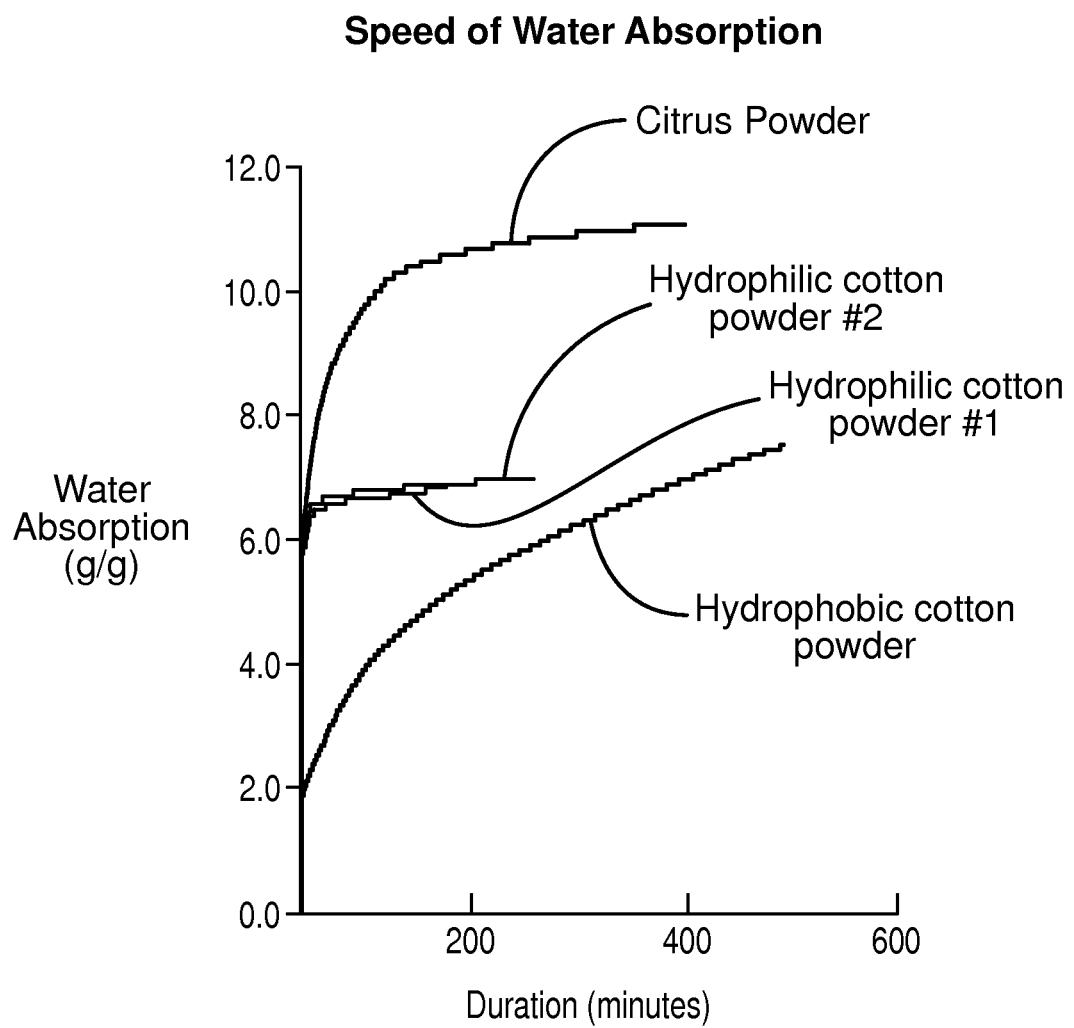
FIG. 4 is a graph of the speed of water absorption measured from various hydrophobic and hydrophilic cotton powders and amphiphilic citrus-derived powder.

As shown in FIG. 4, hydrophobic cotton powder had a slower water absorption rate than hydrophilic cotton powder.

Example 6

Water Absorption Capacity and Oil Absorption Capacity

The water absorption capacity and oil absorption capacity of materials may be determined by the following procedures set forth below in Examples 6A and 6B.

Each experiment was repeated in triplicate for #1 hydrophobic Cotton Particles, hydrophilic Cotton powder (#1), and #2 hydrophobic Cotton Particles.

Example 6A

Measurement of Hydrophobicity and Oil Absorption

Figure 5:
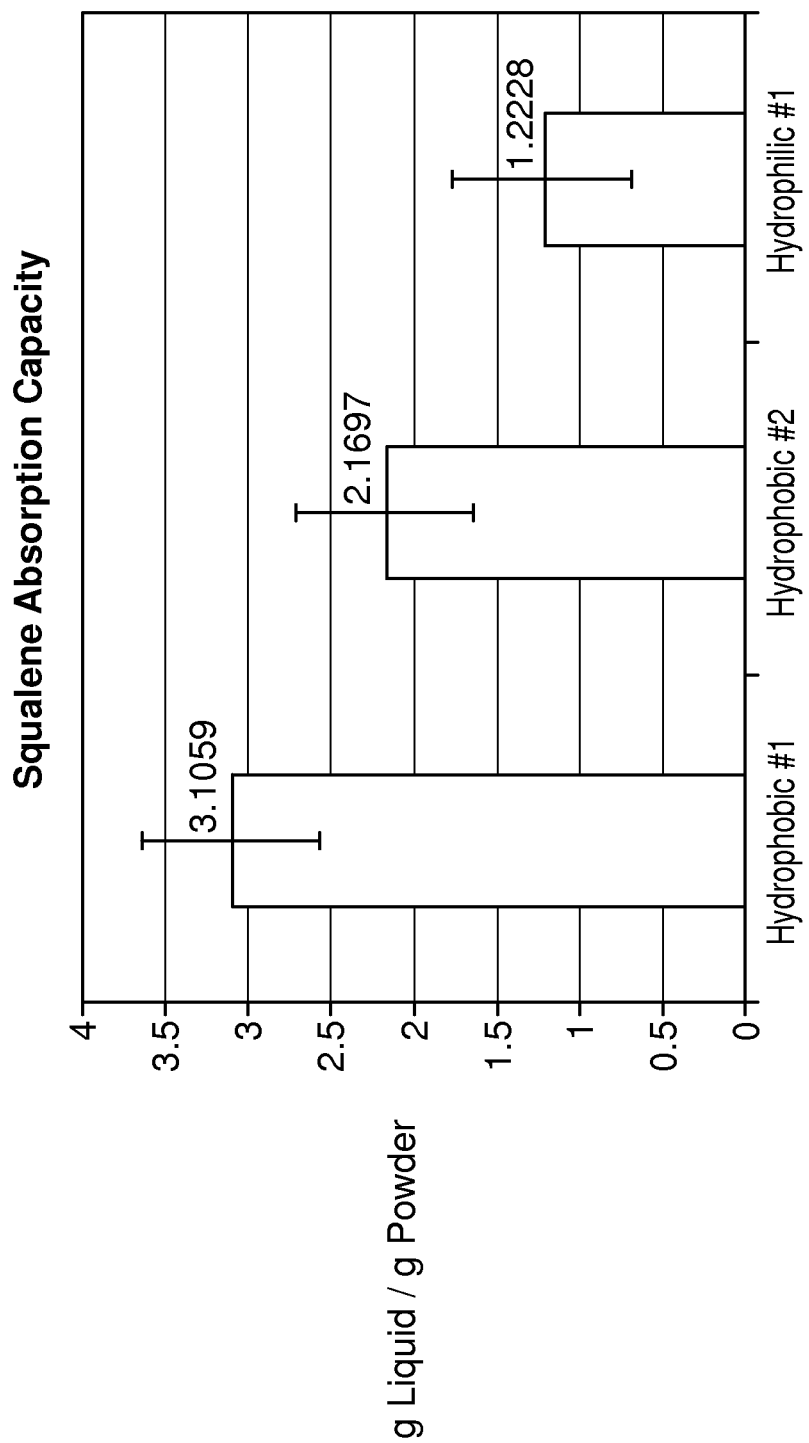
FIG. 5 is a graph illustrating average oil absorption capacity of various hydrophobic and hydrophilic cotton powders.

The scale was tared with the powder samples. Squalene was then added drop by drop via disposable pipette until the sample looked nearly saturated. A metal spatula was used to completely mix in the oil with the powders until saturated (After mixing, the spatula was wiped clean against the side of the weigh boat to ensure there was no loss of material). "Saturation" as used herein is defined as the mixture being able to hold all the available squalene such that the bottom of the boat appeared dry. This determination was based on the appearance of the mixture and the condition of the weigh boat. The total number of grams of squalene was recorded and the relative Oil Absorption ratio was calculated by dividing the total weight of oil by the total weight of cotton materials. The results of performing this procedure are set forth in FIG. 5 hereto.

Example 6B

Measurement of Water Absorption

Figure 6:
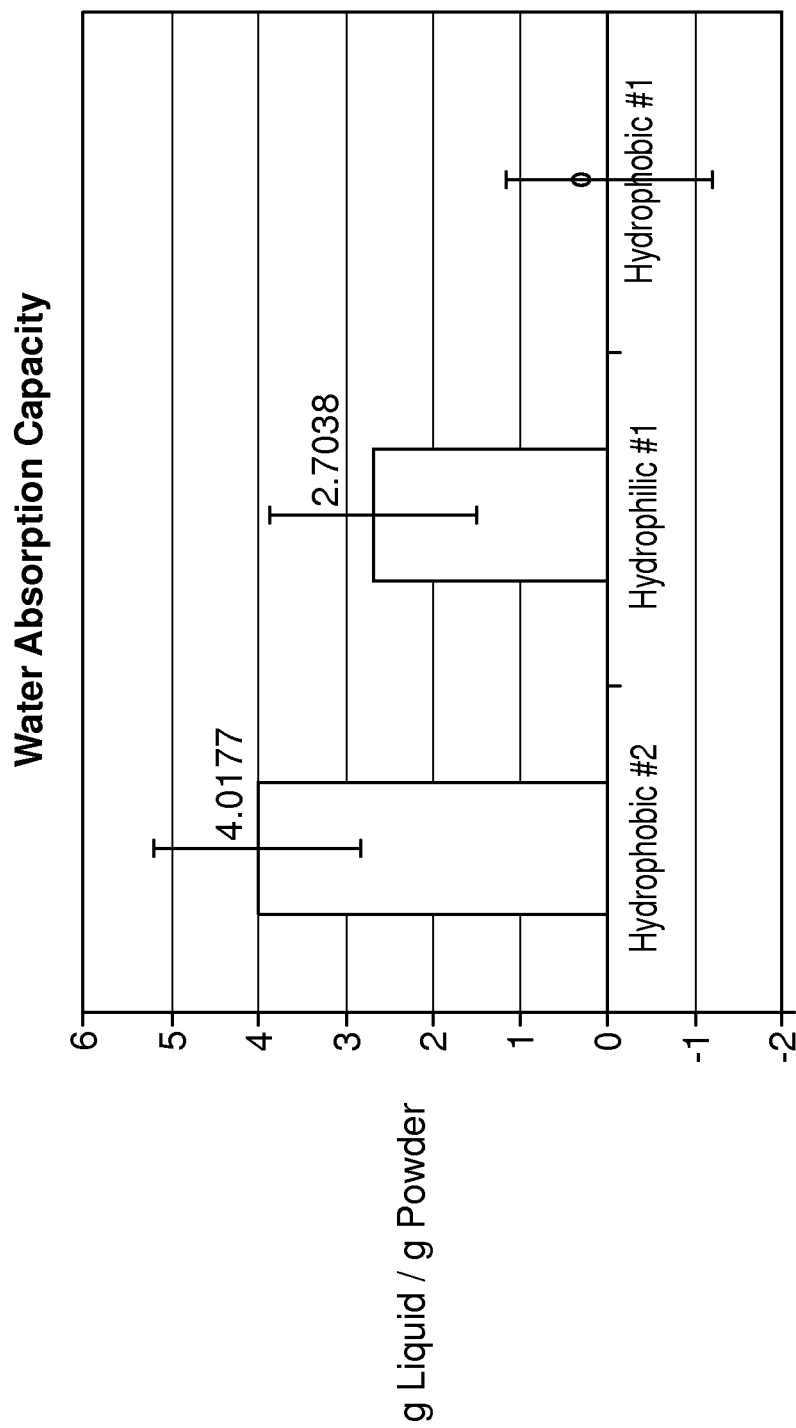
FIG. 6 is a graph illustrating average water absorption capacity of various hydrophobic and hydrophilic cotton powders.

Following a method similar to that described in example 6A, but substituting water for the oil material, water absorption was measured. The results of this test are set forth in FIG. 6.

Example 7

Retention of Oil

The Retention of Oil was determined by the following procedure:

A test site was marked with a circle with 2 cm diameter on an oil impermeable white card. About 6.2 mg of artificial sebum was applied uniformly inside the marked circle to create an oily patch with a Sebumeter reading recorded as pretreatment sebum reading P. Weighed about 25 mg of the test sample and apply it uniformly onto the test site. Measured the sebum within each test with a sebumeter to site and recorded the sebumeter readings 10 minutes after product application. The procedure was repeated for 2 replicas for each test product and the average S was calculated to give the sebum level with product application.

The in-vitro sebum absorption is calculated using the following equation:

% Sebum level change=$(S-P)/P$

Where S=Average Pre-treatment Sebumeter Reading
P=Average Post-treatment Sebum Reading

TABLE 6

| Ingredient(%) | Formula A % | Formula B % | Formula C % |
|---|---|---|---|
| Deionized Water | 87.81 | 85.81 | 85.81 |
| Hydroxyethylcellulose | 0.50 | 0.50 | 0.50 |
| Part #1 | | | |
| Quaternium 91 and Cetrimonium Methosulfate and Cetearyl Alcohol | 1.00 | 1.00 | 1.00 |
| Behenyl Alcohol | 1.50 | 1.50 | 1.50 |
| Stearyl Alcohol | 1.25 | 1.25 | 1.25 |
| Cetyl Alcohol | 3.00 | 3.00 | 3.00 |
| Part #2 | | | |
| Dimethicone | 1.00 | 1.00 | 1.00 |
| Amodimethicone | 0.25 | 0.25 | 0.25 |
| Dimethicone | 2.00 | 2.00 | 2.00 |
| Part #3 | | | |
| Polyquaternium -37 and Propylene Glycol Dicaprate/Dicaprate and PPG-1 Trideceth-6 | 0.20 | 0.20 | 0.20 |
| Phenoxyethanol & Caprylyl Glycol | 1.00 | 1.00 | 1.00 |
| Water (and) Hydrolyzed Lupine Seed Extract | 0.01 | 0.01 | 0.01 |
| Fragrance | 0.35 | 0.35 | 0.35 |
| hydrophobic Cotton Powder(#1) | | 2.00 | |
| Hydrophilic Cotton Powder | | | 2.00 |
| Sodium Hydroxide | 0.13 | 0.13 | 0.13 |
| Total | 100.00 | 100.00 | 100.00 |

The oil absorption in-vitro studies were conducted at the initial and three months' room temperature (RT) storage (22° C.) for the leave-in conditioners listed in the table below. The in-vitro sebum absorption testing showed that the addition of hydrophobic cotton powder (#1) at 2% level in a leave-in conditioner Formulation B increased the sebum absorption in-vitro by 2× times vs. the leave-in conditioner Placebo Formulation A. Formula B of 2% hydrophobic cotton powder (#1) leave-in conditioner has a slightly higher but not significantly different sebum absorption in-vitro than Formulation C of 2% hydrophilic cotton powder leave-in conditioner.

The compositions set forth in Table 6 were prepared in accordance with the following method:
1. Deionized water and hydroxyethylcellulose were added into a mixing container and heated to 75°-80° C.
2. In a separate container, the ingredients set forth in Table 6 above as Part #1 were added and heated to 75°-80° C. until all the ingredients are melted. 3. After all of Part #1 ingredients were melted, the hydroxyethylcellulose solution was phased with Part #1 and mixed until homogeneous. Cooling to below 40° C. was then begun.
4. At 60°-65° C. the Part #2 ingredients were added one at a time allowing for good mixing and mixed until the batch was homogeneous.
5. At or below 40° C. the Part #3 ingredients were added.
6. In a separate container, sodium hydroxide and DI water were premixed and the pH of the batch adjusted to pH 4.0-4.5.
7. The ingredients were adjusted to 100% weight per weight in the batch and the batch was homogenized for 1-5 minutes.
8. The cotton powder was added and the batch mixed until it was homogeneous.

Figure 7:
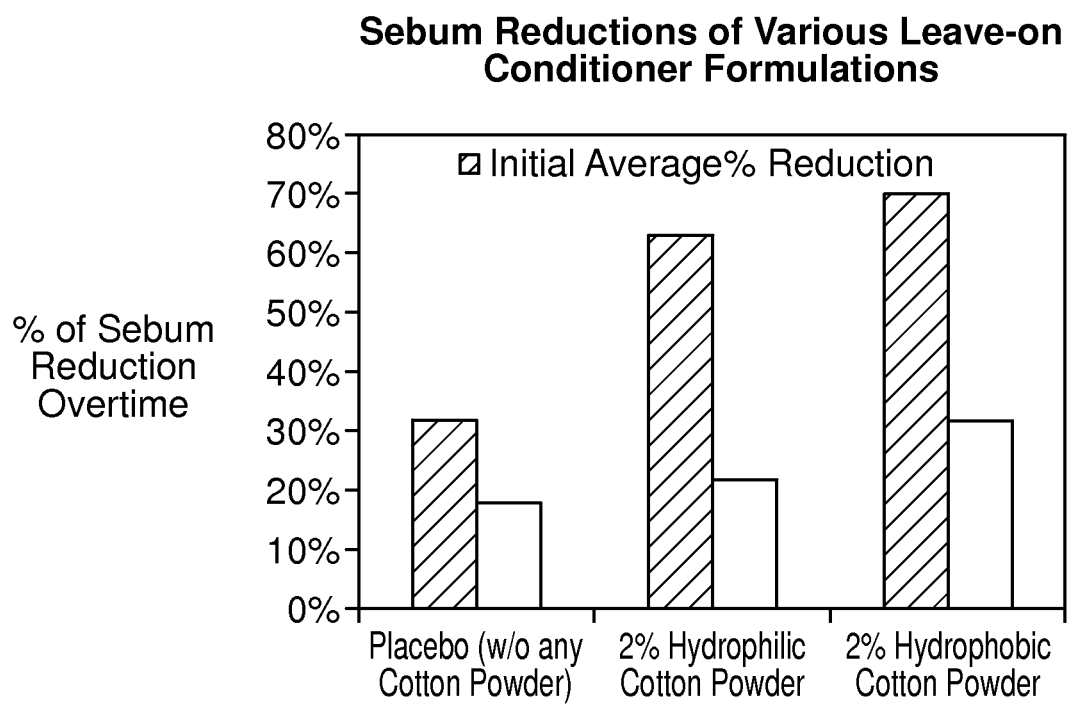
FIG. 7 is a graph illustrating sebum reduction of various cleanser formulations containing cotton powder.

The degree of sebum absorption resulting from the above-mentioned procedure for each composition (Formulations A through C) is reflected in the graph set forth in FIG. 7 hereto. As shown therein, hydrophobic cotton powder retained a significantly higher amount of oil (i.e., sebum) for leave-in hair conditioning compositions than compositions containing Hydrophilic cotton powder.

Example 8

Cleansing Compositions

TABLE 7

| INCI Name | Example 8a | Example 8b | Example 8c | Example 8d | Example 8e | Example 8f |
| --- | --- | --- | --- | --- | --- | --- |
| Water | QS | QS | QS | QS | QS | QS |
| Glycerin | 0.00-15.00 | 0.00-15.00 | 0.00-15.00 | 0.00-15.00 | 0.00-15.00 | 0.00-15.00 |
| Acrylates Copolymer | 0.00-12.00 | — | — | — | — | — |
| Acrylates/C10-30 Alkyl Acrylate Crosspolymer | — | — | — | — | 0.00-1.00 | — |
| Carbomer | — | — | — | — | — | 0.00-1.00 |
| Xanthan Gum | — | — | — | 0.00-2.00 | — | — |
| Sodium Laureth Sulfate | 0.00-40.00 | — | — | — | 0.00-40.00 | 0.00-40.00 |
| Decyl Glucoside | — | 0.00-14.00 | — | 0.00-14.00 | — | — |
| Lauryl Glucoside | — | 0.00-17.00 | — | — | 0.00-17.00 | 0.00-17.00 |
| Ammonium Laureth Sulfate | — | 0.00-16.00 | — | — | — | — |
| Cocamidopropyl Betaine | 0.00-17.00 | — | — | 0.00-17.00 | 0.00-17.00 | 0.00-17.00 |
| Cocamide MEA | — | 0.00-1.00 | — | — | — | — |
| Glycereth-7 | — | 0.00-5.00 | — | — | — | — |
| PPG-2 Hydroxyethyl Cocamide | — | — | — | 0.00-2.00 | — | — |
| PEG-16 Soy Sterol | — | — | — | 0.00-2.00 | 0.00-2.00 | 0.00-2.00 |
| PEG-120 Methyl Glucose Dioleate | — | 0.00-1.60 | 0.00-2.00 | — | — | — |
| PEG-80 Sorbitan Laurate | — | — | 0.00-3.00 | — | — | — |
| Cocamidopropyl PG dimonium Chloride Phosphate | — | — | 0.00-2.00 | — | — | — |
| Sodium C14-16 Olefin Sulfonate | — | — | 0.00-40.00 | — | — | — |
| Disodium Lauroamphodiacetate | — | — | 0.00-5.00 | 0.00-5.00 | — | — |
| Sodium Cocoyl Sarcosinate | — | — | 0.00-5.00 | — | — | — |
| C12-15 Alkyl Lactate | — | — | 0.00-1.00 | — | — | — |
| Glycol Stearate | — | 0.00-2.00 | — | — | 0.00-2.00 | 0.00-2.00 |
| Glycol Distearate | — | — | — | — | 0.00-2.00 | 0.00-2.00 |
| Laureth-4 | — | — | — | — | 0.00-2.00 | 0.00-2.00 |
| Salicylic Acid | — | — | 0.00-2.00 | — | — | — |
| EDTA | 0.00-0.40 | 0.00-0.40 | 0.00-0.40 | 0.00-0.40 | 0.00-0.40 | 0.00-0.40 |
| Preservative | 0.00-2.00 | 0.00-2.00 | 0.00-2.00 | 0.00-2.00 | 0.00-2.00 | 0.00-2.00 |
| Citric Acid | QS to adjust pH | QS to adjust pH | QS to adjust pH | QS to adjust pH | QS to adjust pH | QS to adjust pH |
| Sodium Hydroxide | QS to adjust pH | QS to adjust pH | QS to adjust pH | QS to adjust pH | QS to adjust pH | QS to adjust pH |
| Polyethylene | 0.00-2.00 | 0.00-2.00 | 0.00-2.00 | 0.00-2.00 | 0.00-2.00 | 0.00-2.00 |
| Fragrance | 0.00-1.00 | 0.00-1.00 | 0.00-1.00 | 0.00-1.00 | 0.00-1.00 | 0.00-1.00 |
| Cotton Powder Hydrophobic | 0.00-20.00 | 0.00-20.00 | 0.00-20.00 | 0.00-20.00 | 0.00-20.00 | 0.00-20.00 |

TABLE 7-continued

| INCI Name | Example 8a | Example 8b | Example 8c | Example 8d | Example 8e | Example 8f |
|---|---|---|---|---|---|---|
| Cotton Powder Hydrophilic | 0.00-20.00 | 0.00-20.00 | 0.00-20.00 | 0.00-20.00 | 0.00-20.00 | 0.00-20.00 |
| Citrus Powder | 0.00-20.00 | 0.00-20.00 | 0.00-20.00 | 0.00-20.00 | 0.00-20.00 | 0.00-20.00 |

Cleansing compositions of this invention may be made in accordance with the following procedure:
1. Add water to a vessel and begin mixing.
2. Add Acrylates copolymer or acrylates/C10-30 Alkyl Acrylate Crosspolymer or Carbomer or Xanthan Gum to the vessel and mix until completely dispersed.
3. Neutralize Carbomer with sodium hydroxide.
4. Add Sodium Laureth Sulfate and/or Decyl Glucoside and/or Lauryl Glucoside and/or Ammonium Laureth Sulfate to the vessel.
5. Add Cocamidopropyl betaine (pre-dispersed salicylic acid, if necessary, in cocoamidopropyl betaine) and/or Cocamide MEA and/or Glycereth-7 and/or PPG-2 Hydroxyethyl Cocamide and/or PEG-16 Soy Sterol and/or PEG-120 Methyl Glucose Dioleate to the vessel.
6. Add PEG-80 Sorbitan Laurate and/or Cocamidopropyl PG dimonium chloride phosphate and/or Sodium C14-16 Olefin Sulfonate and/or Disodium Lauroamamphodiacetate and/or Sodium cocoyl Sarcosinate and/or PEG-120 Methyl Glucose Dioleate to the vessel and mix.
7. Add Glycol Stearate and/or Glycol Distearate and/or Laureth-4 and/or C12-15 Alkyl Lactate and mix the ingredients.
8. Add EDTA and Preservative to the vessel and mix.
9. Add polyethlene and fragrance and mix.
10. Adjust the pH of the formulation to the desired pH using sodium hydroxide and/or citric acid.
11. Add hydrophobic cotton powder and/or hydrophilic cotton powder to the mixture.

Example 9

Sebum Absorption Study Using Cleansing Composition

A baseline reading of sebum quantity was taken from selected skin testing sites on the skin surface of nine subjects (Three points—opposite ends and in the middle of the forehead) prior to wetting the skin with water from running faucet. The sebum quantity was measured using a sebumeter. 0.5 cc gel Cleanser (placebo) was applied to skin then the skin massaged for ten seconds. Water was added to the skin and the skin was lathered for additional twenty seconds. Cleanser was rinsed from the skin and any excess residue with water for thirty seconds then blot dried with a Kimwipe.

These steps were repeated with hydrophobic and hydrophilic cotton powders as shown in Table 8 and excess moisture permitted to air dry for about five minutes.

After washing by taking two points spaced out for both the placebo and cotton prototype, sebum count was measured with a sebumeter cartridge consecutively 4 hours and 6 hours after washing, respectively.

For accuracy, each sebum count should be conducted on a fresh skin area (i.e. the same area cannot be measured more than once). Once sebum is measured by the sebumeter cartridge, that particular site will have been disrupted so as to affect accuracy of the measurement of sebum as sebum is produced throughout the day on the skin.

Figure 8:
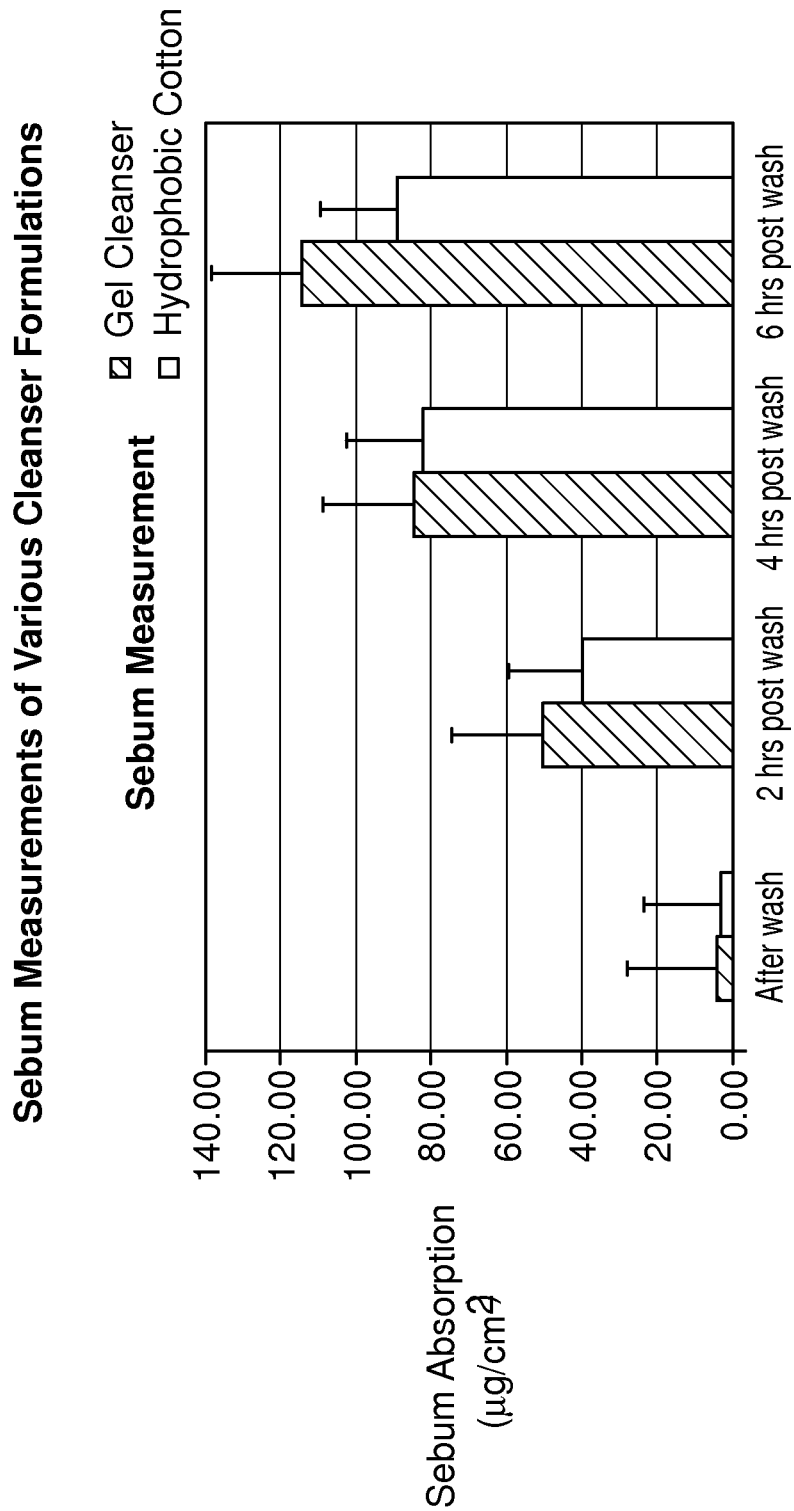
FIG. 8 is a graph illustrating average sebum measurements of various cleanser formulations over time.
Figure 9:
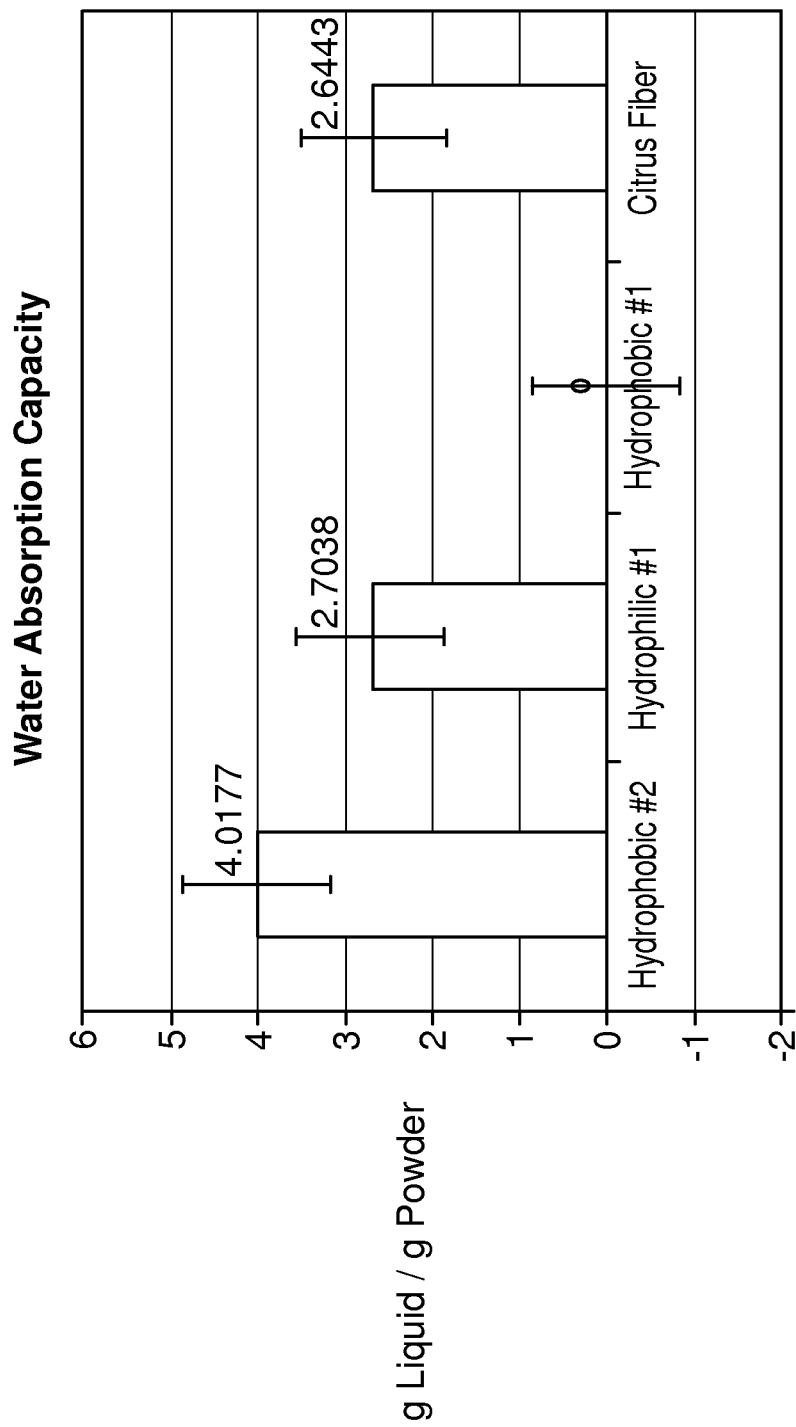
FIG. 9 is a graph illustrating average water absorption capacity of several cellulose powders.
Figure 10:
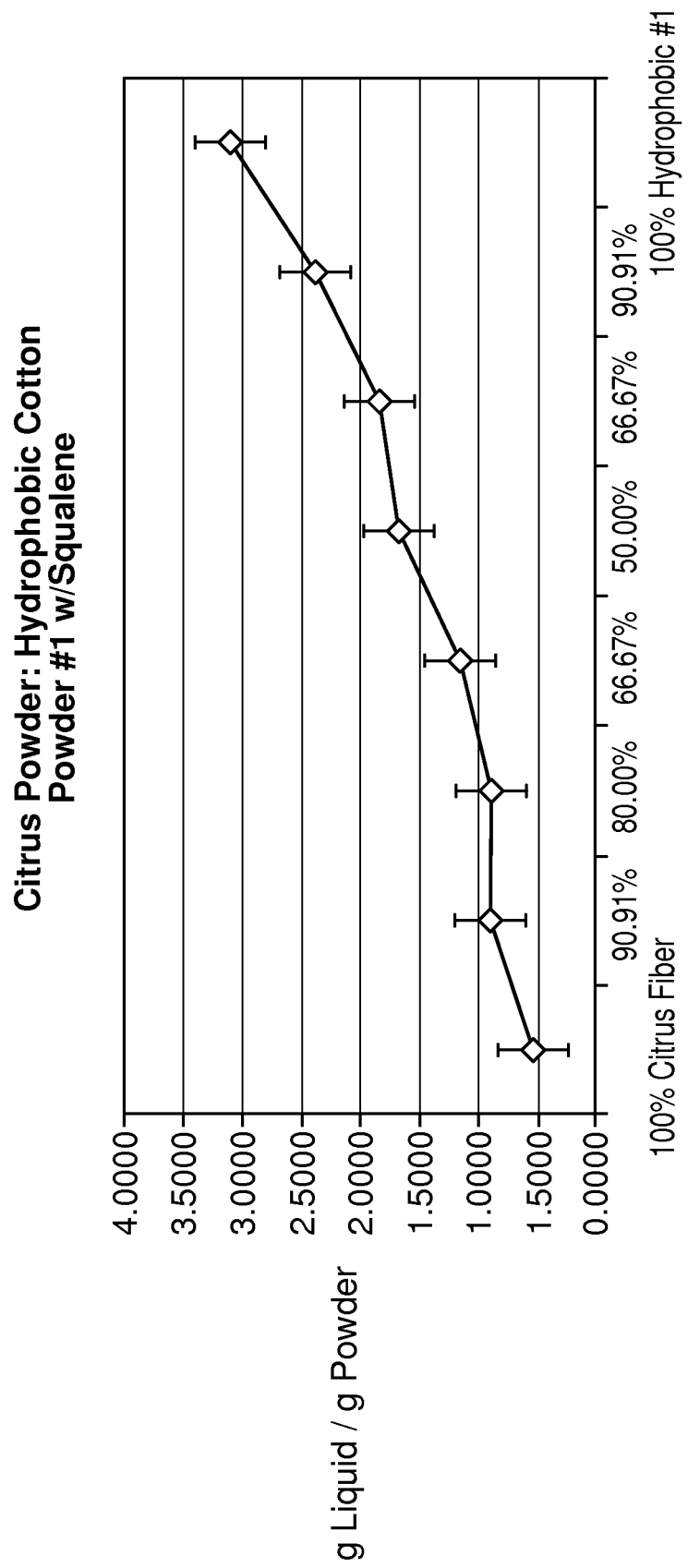
FIG. 10 is a graph illustrating absorption of squalene by compositions containing hydrophobic cotton and citrus-derived powders.
Figure 11:
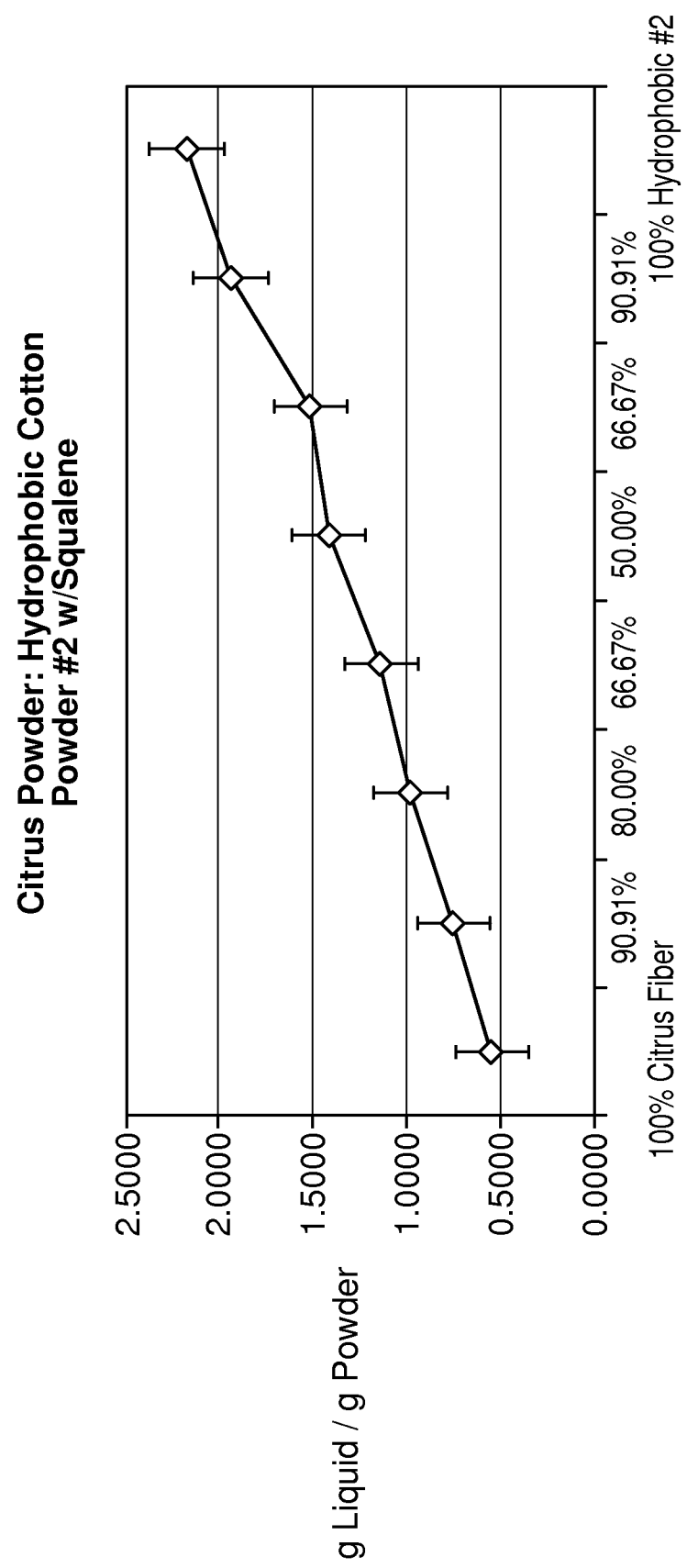
FIG. 11 is a graph illustrating absorption of squalene by compositions containing hydrophobic cotton and citrus-derived powders.
Figure 12:
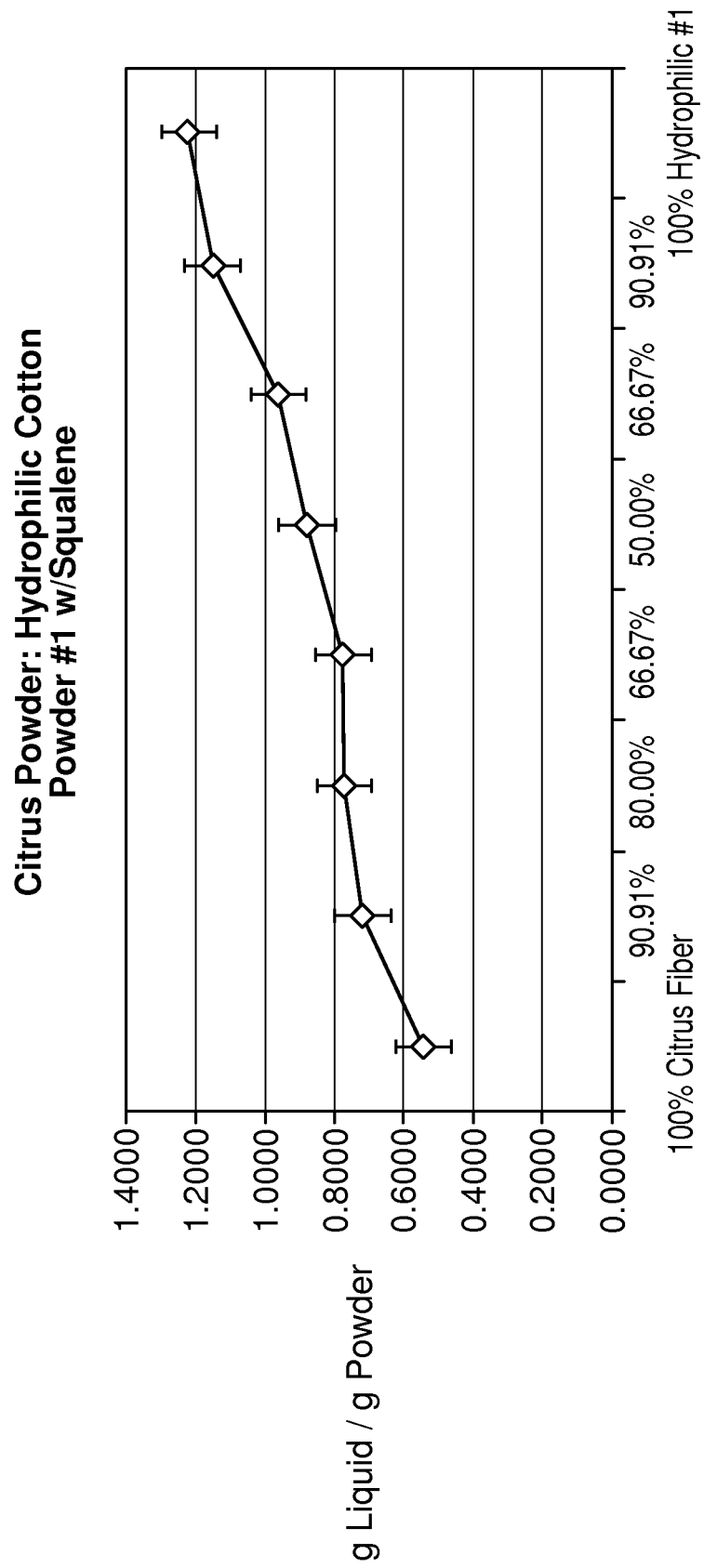
FIG. 12 is a graph illustrating absorption of squalene by compositions containing hydrophilic cotton and citrus-derived powders.
Figure 13:
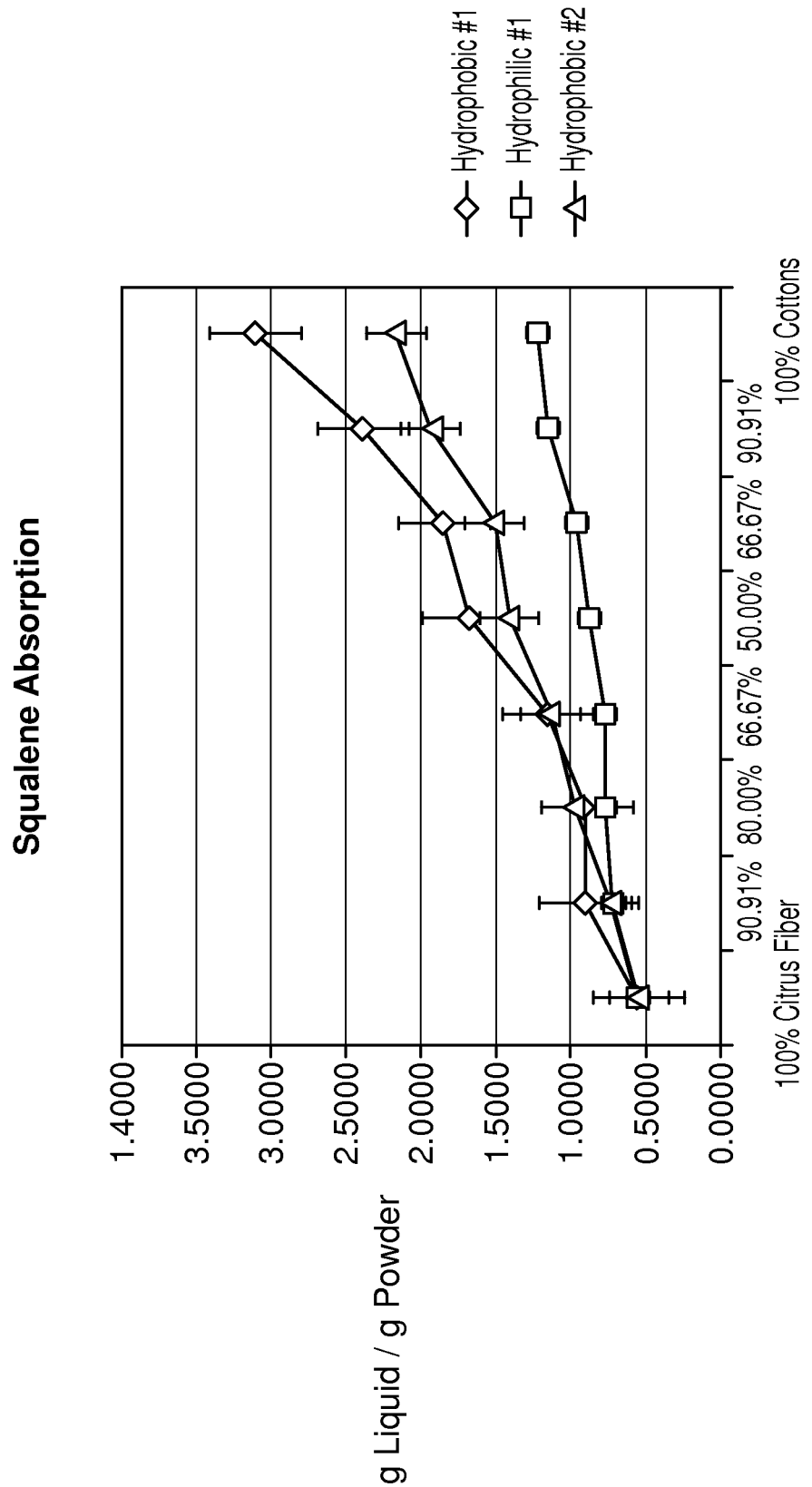
FIG. 13 is a graph illustrating comparative oil absorption of combinations of citrus-derived and cotton powders in varying amounts.
Figure 14:
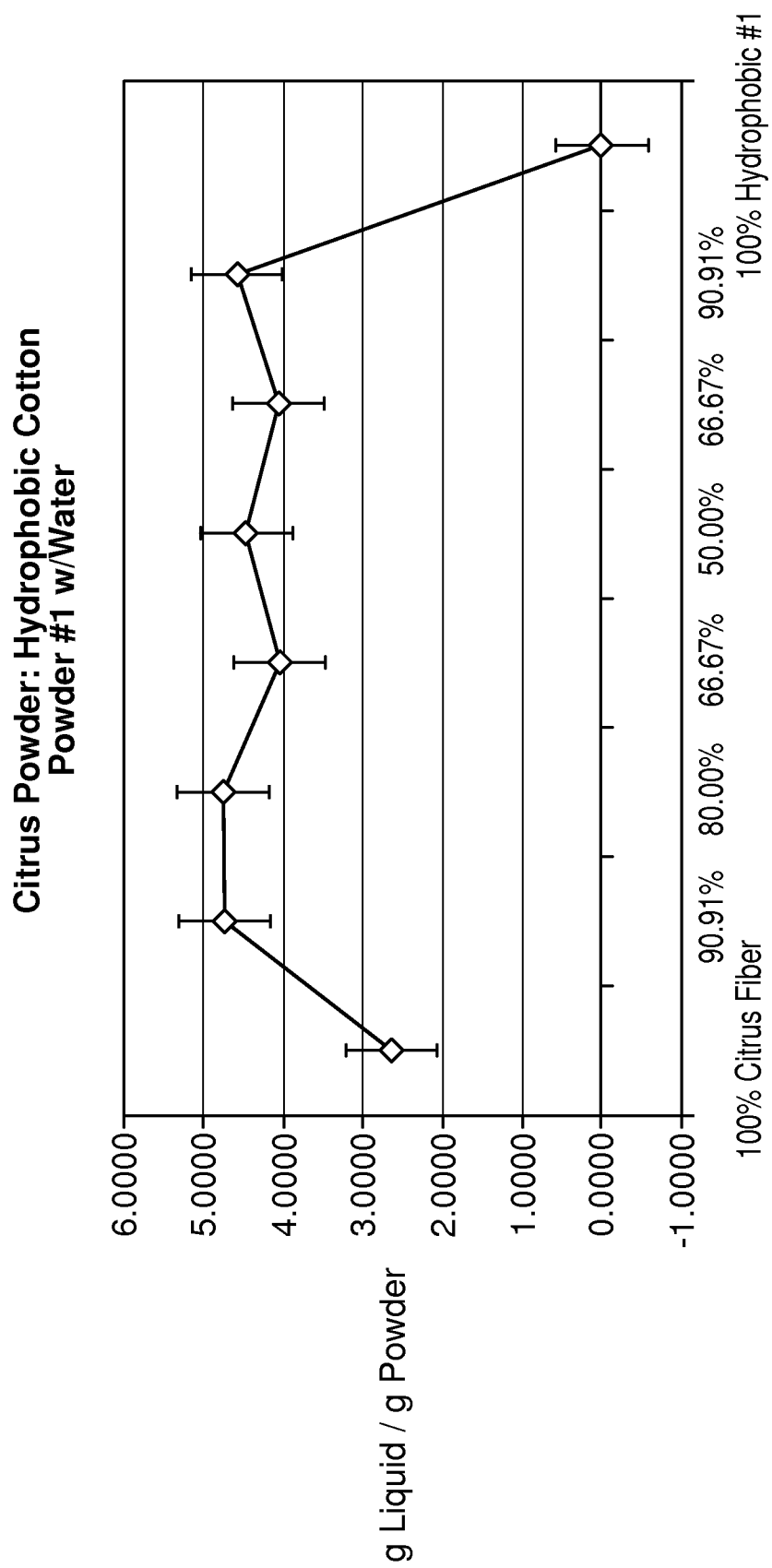
FIG. 14 is a graph illustrating water absorption by compositions containing hydrophobic cotton and citrus-derived powders.
Figure 15:
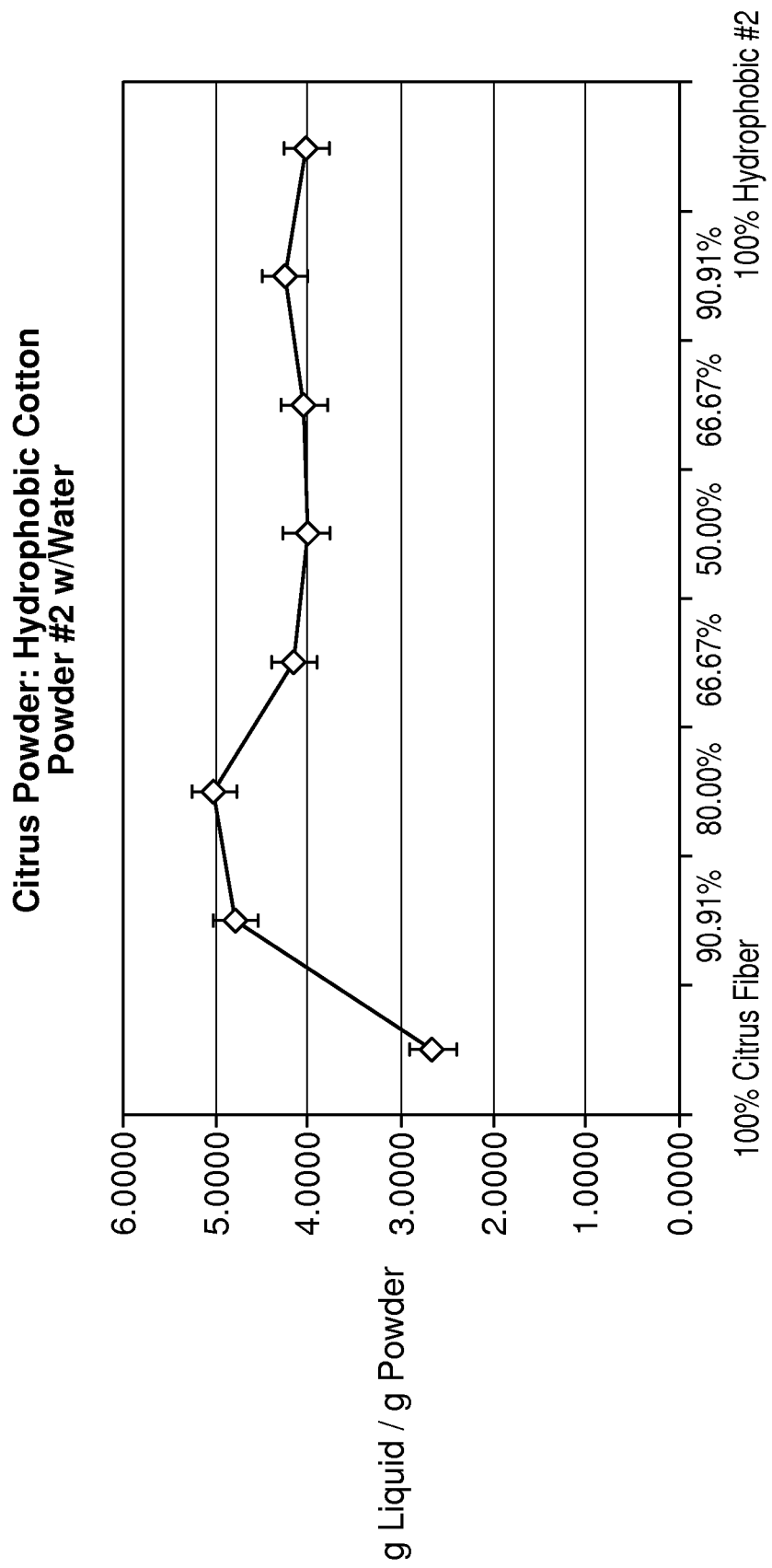
FIG. 15 is a graph illustrating water absorption by compositions containing hydrophobic cotton and citrus-derived powders.
Figure 16:
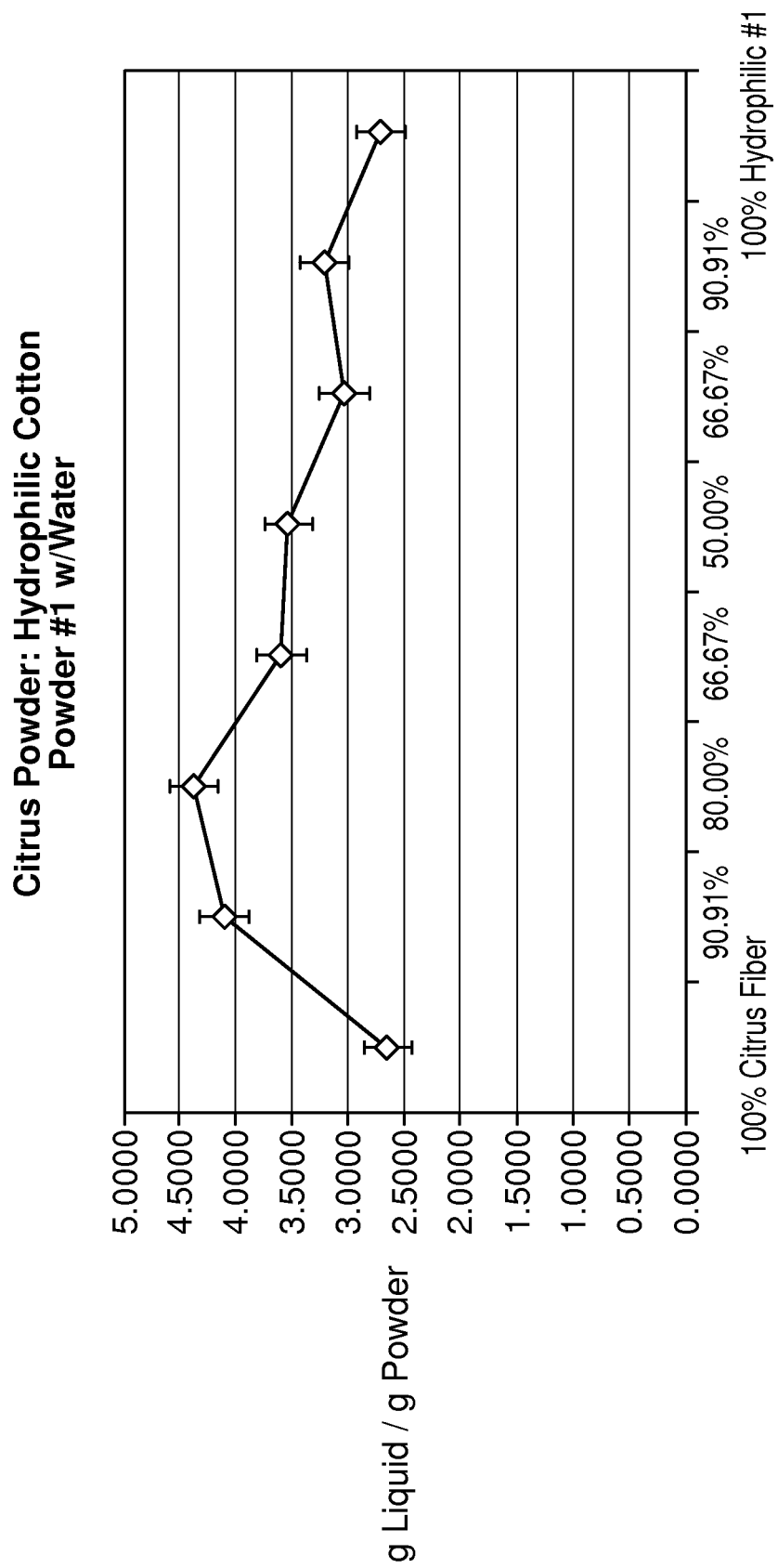
FIG. 16 is a graph illustrating water absorption by compositions containing hydrophilic and citrus-derived powders.
Figure 17:
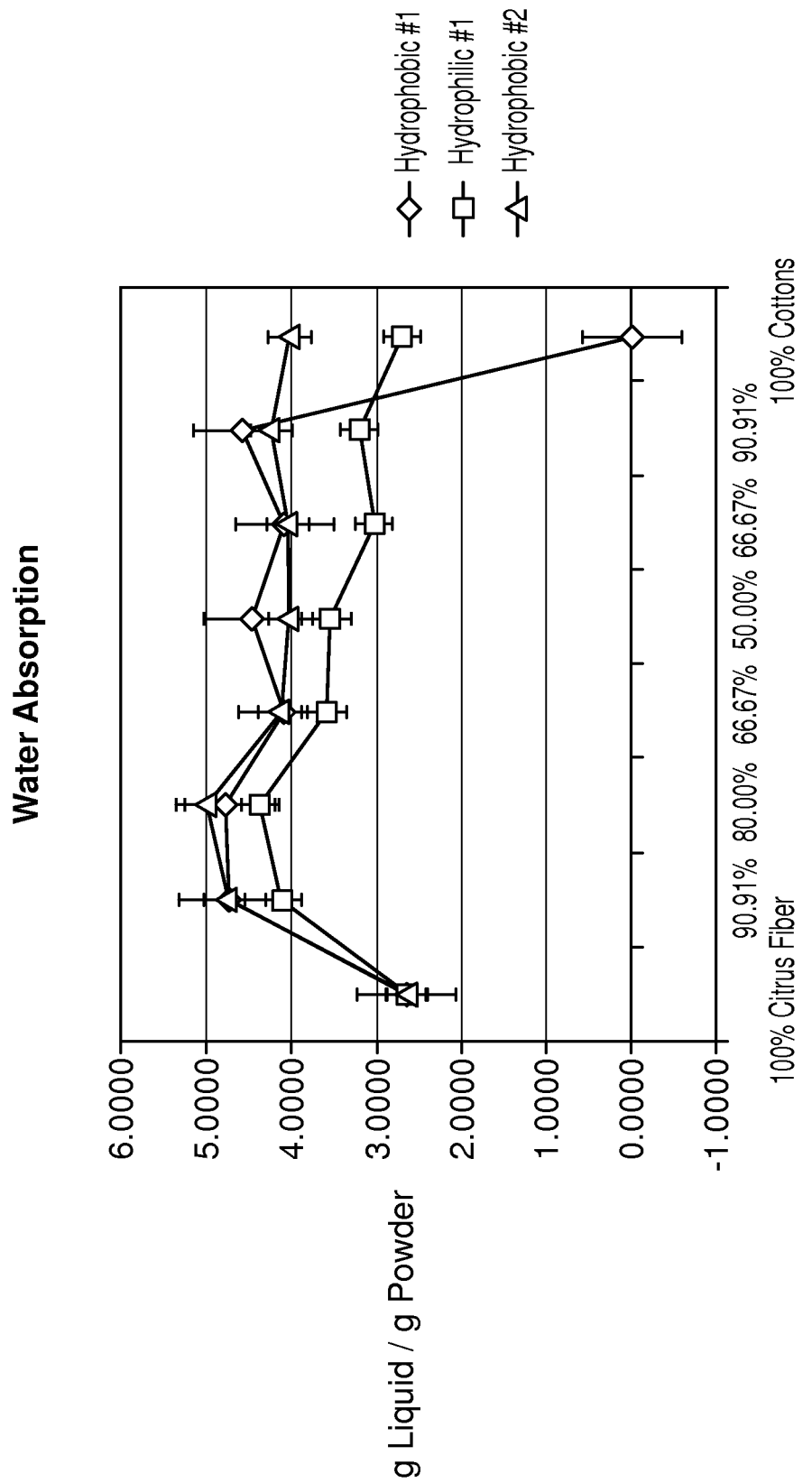
FIG. 17 is a graph illustrating comparative water absorption of combinations of citrus-derived and cotton powders in varying amounts.

Results of the sebum absorption measurements for Example 9A and 9B are set forth in FIG. 8 hereto (Example 9C was not tested in this example). As can be observed from the graph in FIG. 8, sebum production of skin cleansed with composition containing hydrophobic and hydrophilic cotton powders was slowed as compared with that cleansed with a gel cleanser.

TABLE 8

| Ingredient Trade Name | CTFA/INCI Name | Example 9A (Gel Cleanser) % w/w | Example 9B Hydrophilic Cotton % w/w | Example 9C Hydrophobic Cotton % w/w |
|---|---|---|---|---|
| Purified Water | Water | 54.08 | 48.71 | 49.26 |
| Rhodapex ES-2K | Sodium Laureth Sulfate; Water | 29.00 | 29.00 | 29.00 |
| Glycerin 99.7% USP | Glycerin | 3.00 | 3.00 | 3.00 |
| TEGO Betain F50 | Cocamidopropyl Betaine | 4.00 | 4.00 | 4.00 |
| Sodium Hydroxide | Sodium Hydroxide | 0.32 | 0.32 | 0.32 |
| Edetate Disodium USP | Disodium EDTA | 0.20 | 0.20 | 0.20 |
| Optiphen | Phenoxyethanol (and) Caprylyl Glycol | 1.00 | 0.00 | 0.00 |
| Phenonip XB | Phenoxyethanol; Methylparaben; Ethylparaben; Propylparaben | 0.28 | 0.00 | 0.00 |
| Phenoxetol | Phenoxyethanol | 0.00 | 0.60 | 0.60 |

TABLE 8-continued

| Ingredient Trade Name | CTFA/INCI Name | Example 9A (Gel Cleanser) % w/w | Example 9B Hydrophilic Cotton % w/w | Example 9C Hydrophobic Cotton % w/w |
|---|---|---|---|---|
| Spectrastat | Caprylyl Glycol (and) Caprylhydroxamic Acid | 0.00 | 0.00 | 0.50 |
| Optiphen | Phenoxyethanol (and) Caprylyl Glycol | 0.00 | 0.80 | 0.00 |
| Chlorphensin | Chlorphensin | 0.00 | 0.25 | 0.00 |
| Citric Acid Anhydrous Fine Granular USP | Citric Acid | 0.12 | 0.12 | 0.12 |
| Hydrophilic Cotton | Cotton Powder | 0.00 | 5.00 | 0.00 |
| Hydrophobic Cotton | Cotton Powder | 0.00 | 0.00 | 5.00 |
| Carbopol Aqua SF-1 Polymer | Acrylates Copolymer | 8.00 | 8.00 | 8.00 |
| | Total | 100.00 | 100.00 | 100.00 |

Example 10

Citrus-Cotton Combination Compositions

Using the materials set forth below, compositions containing cotton particle and citrus particle were made in accordance with the following procedure.

Citrus particles and Cotton particles were blended in ratios as specified in the following table and as specified below:

| Citrus Particles (g) | Cotton Particles (g) | Ratio of Citrus Particles to Cotton Particles |
|---|---|---|
| 0.2 | 0.2 | 1:1 |
| 0.2 | 0.1 | 2:1 |
| 0.2 | 0.05 | 4:1 |
| 0.1 | 0.2 | 1:2 |
| 0.02 | 0.2 | 1:10 |
| 0.2 | 0.02 | 10:1 |

Citrus particles were placed into a tared weighing boat with the exact weight recorded, followed by Cotton particles (IFC, Goonvean, and RON) in accordance to each of the ratios above. The Citrus particle and cotton particles were then thoroughly mixed together with a metal spatula. Once the Cotton particles were uniform with the Citrus Particle, the scale was tared with the blended particles sample. Squalene was then added drop by drop via disposable pipette until the sample looked nearly saturated. A metal spatula was used to completely mix in the oil with the particles until saturated. After mixing, the spatula was wiped clean against the side of the weigh boat to ensure there was no loss of material. "Saturation" as used herein is defined as the mixture being able to hold all the available squalene such that the bottom of the boat appeared dry. This determination was based on the appearance of the mixture and the condition of the weigh boat.

The total number of grams of squalene was recorded and the relative Oil Absorption ratio was calculated by dividing the total weight of oil by the total weight of citrus particle/cotton particles blend. The results of these measurements are set forth in FIGS. 9 through 13 hereto.

Following a similar method as described above, water absorption for the particles blends was also measured. The results of these measurements are set forth in FIGS. 14 through 17 hereto.

As shown in FIGS. 14 through 17, pure citrus particles exhibit the superior water absorption, while pure cotton particles exhibit excellent oil absorption properties. Surprisingly and unexpectedly, the combination of citrus and cotton particles show both excellent water absorption and oil absorption properties.

What is claimed is:

1. A skin care composition, comprising:
   (a) regenerated hydrophobic linear cellulose particles having an average length of about 1000 µm, a particle aspect ratio from about 1000 to about 2 and a thickness of from about 1 to about 500 µm; (b) amphiphilic linear cellulose particles derived from sources selected from the group consisting of citrus pulp, sugar beet pulp, banana pulp, mango pulp, apple pulp, passion fruit pulp and tomato pulp, said amphiphilic linear cellulose particles having an average size of from about 1 to about 1000 µm, a particle aspect ratio from about 1000 to about 2 and a thickness of from about 1 to about 500 µm; and (c) a cosmetically acceptable carrier; wherein the ratio of said amphiphilic linear cellulose particles to said regenerated hydrophobic linear cellulose particles is from about 1:10 to about 10:1.

2. The skin care composition according to claim 1 wherein said composition further comprises at least one cleansing agent selected from the group consisting of a saponified fat and a surfactant.

3. The skin care composition according to claim 1 wherein said regenerated hydrophobic linear cellulose particles have an oil absorption capacity and retention of from about 150 to about 500% by weight oil/weight particles.

4. The skin care composition according to claim 3 wherein said oil absorption capacity and retention of said regenerated hydrophobic linear cellulose particles is from about 300 to about 500% by weight oil/weight particles.

5. The skin care composition according to claim 1 wherein the water contact angle of said regenerated hydrophobic linear cellulose particles is greater than 90 degrees.

6. The skin care composition according to claim 5 wherein said water contact angle of said regenerated hydrophobic linear cellulose particles is greater than about 100 degrees.

7. The skin care composition according to claim 6 wherein said water contact angle of said regenerated hydrophobic linear cellulose particles is greater than about 120 degrees.

8. The skin care composition according to claim 1 wherein said regenerated hydrophobic linear cellulose particles are coated with a hydrophobic agent selected from the group consisting of metal soap, organic wax, synthetic wax, long-chain fatty acids, long-chain fatty esters, non-water soluble polymers, high molecular water-insoluble fluoropolymers, and polymerized siloxanes.

9. The skin care composition according to claim 1 wherein said ratio of said regenerated hydrophobic linear cellulose particles to said amphiphilic linear cellulose particles is from about 1:1 to about 4:1.

10. The skin care composition according to claim 1 wherein said ratio of said regenerated hydrophobic linear cellulose particles to said amphiphilic linear cellulose particles is from about 1:1 to about 2:1.

11. The skin care composition according to claim 1 wherein the size of said regenerated hydrophobic linear cellulose particles is from about 2 to about 300 μm.

12. The skin care composition according to claim 1 wherein said amphiphilic linear cellulose particles are derived from citrus pulp.

13. The skin care composition according to claim 1 wherein said composition further comprises at least one emollient.

14. The skin care composition according to claim 1 wherein said composition comprises from about 1 to about 20 percent by weight of said regenerated hydrophobic linear cellulose particles.

15. The skin care composition according to claim 1 wherein said composition comprises from about 1 to about 10 percent by weight of said regenerated hydrophobic linear cellulose particles.

16. The skin care composition according to claim 1 wherein said composition comprises from about 1 to about 6 percent by weight of said regenerated hydrophobic linear cellulose particles.

17. The skin care composition according to claim 1, wherein said composition is a rinse-off cleanser.

* * * * *